(12) United States Patent
Trocki et al.

(10) Patent No.: US 6,585,700 B1
(45) Date of Patent: Jul. 1, 2003

(54) SYRINGE, SYRINGE PLUNGER AND ATTACHMENT MECHANISM FOR FRONT LOADING MEDICAL INJECTOR

(75) Inventors: Mark Trocki, Cheswick, PA (US); Michael J. Masters, Jeannette, PA (US)

(73) Assignee: Medrad, Inc., Indianola, PA (US)

( * ) Notice: Subject to any disclaimer, the term of this patent is extended or adjusted under 35 U.S.C. 154(b) by 26 days.

(21) Appl. No.: 09/679,850

(22) Filed: Oct. 5, 2000

(51) Int. Cl.7 .............................................. A61M 5/315
(52) U.S. Cl. ........................ 604/218; 604/219; 604/287
(58) Field of Search ............................... 604/218, 222, 604/219, 220, 221, 287, 187, 230, 228, 229

(56) References Cited

U.S. PATENT DOCUMENTS

| | | | |
|---|---|---|---|
| 4,636,198 A | * | 1/1987 | Stade .......................... 604/154 |
| 5,397,313 A | * | 3/1995 | Gross .......................... 604/218 |
| 5,738,659 A | | 4/1998 | Neer et al. |
| 5,865,805 A | | 2/1999 | Ziemba |
| 5,868,710 A | | 2/1999 | Battiato et al. |
| 5,873,861 A | * | 2/1999 | Hitchins et al. ............. 604/218 |
| 5,902,276 A | * | 5/1999 | Namey, Jr. ................... 604/218 |
| 5,913,844 A | | 6/1999 | Ziemba et al. |
| 5,925,022 A | | 7/1999 | Battiato et al. |
| 5,928,197 A | | 7/1999 | Niehoff |
| 5,997,502 A | | 12/1999 | Reilly et al. |
| 6,017,330 A | * | 1/2000 | Hitchins et al. ............. 604/218 |
| 6,048,334 A | | 4/2000 | Hirschman et al. |
| 6,090,064 A | | 7/2000 | Reilly et al. |
| 6,224,577 B1 | * | 5/2001 | Dedola et al. ............... 604/218 |

* cited by examiner

*Primary Examiner*—Gregory Huson
*Assistant Examiner*—Khoa D. Huynh
(74) *Attorney, Agent, or Firm*—Gregory L. Bradley; Henry E. Bartony

(57) ABSTRACT

A mounting member for attaching a front-loading syringe to a powered injector is disclosed. The present invention may also include a plunger that has a two-piece molded core portion that is readily attachable to a plunger drive member of a powered injector. The plunger core may also be equipped with an anti-cocking flange to prevent the plunger from being axially misaligned within the syringe body which could result in fluid leakage between the plunger and the syringe body. An alignment flange may also be provided on the plunger to assist with the proper insertion of the plunger into the syringe during the assembly process. A method of manufacturing a syringe plunger is also disclosed. The present invention further includes a sleeve for clampingly engaging a heating blanket to the outer surface of a syringe.

56 Claims, 19 Drawing Sheets

SYRINGE, SYRINGE PLUNGER AND ATTACHMENT MECHANISM FOR FRONT LOADING MEDICAL INJECTOR

CROSS-REFERENCE TO RELATED APPLICATIONS

Not applicable.

FEDERALLY SPONSORED RESEARCH

Not applicable.

BACKGROUND OF THE INVENTION

The subject invention relates to medical syringes and syringe actuation apparatuses and more particularly to front-loading medical injectors and syringes for use therewith.

Syringe injection systems have been used in medical procedures for many years. Many such syringes are operated by manually advancing a plunger slidably received within the syringe to pressurize the fluid within the syringe and expel it from the syringe through an opening in the forward end of the syringe. In numerous medical injection procedures, however, accurate control and/or high pressures are required that cannot be achieved via manual syringe operation.

Over the years, a number of syringes and powered injectors for actuating the syringes have been developed for use in medical procedures such as angiography, computed tomography, ultrasound and NMR/MRI. A powered injector typically includes a housing that operably supports a drive member that is constructed for attachment to a plunger contained within a syringe. Many powered injectors contain varying levels of sophisticated control circuitry for controlling the advancement and retraction of the plunger drive member.

Depending upon the pressures required by the injection procedure, some injectors are equipped with pressure jackets for supporting and preventing the body of the syringe from bursting during the injection procedure. Examples of such injectors are disclosed in U.S. Pat. Nos. 5,928,197; 5,865,805; 5,300,031 and 5,738,659. In these devices, the syringe is inserted into the open end of a pressure jacket that is affixed to a mounting plate that is connected to the front of the injector housing. The forward portion of the syringe is equipped with an attachment flange that is formed with threadlike flanges for engagement with corresponding flanges provided around the open forward end of the pressure jacket. The mounting plate is typically pivotally and removably attached to the front of the injector housing. Prior to operation, the mounting plate must be locked to the injector housing by rotating a locking mechanism into locking engagement with a forward protruding pin mounted to the injector housing. Such injectors may also be equipped with sensors positioned within the injector housing and arranged to detect a magnet positioned in a certain position within the mounting plate to inform the control circuit of the type of mounting plate (and corresponding syringe size) that is attached to the injector. Thus, it will be appreciated that such locking mechanism and pressure jacket arrangement can be expensive to manufacture and cumbersome to use. Accordingly, there is a need for a mechanism for attaching a front-loading syringe to a powered injector that does not require the use of expensive and cumbersome locking mechanisms for locking the syringe mounting plate in an injection position.

Syringes that are constructed for use with powered injectors include a plunger for forcing the fluid medium contained within the syringe body through an opening in the forward end of the syringe. Such plungers typically comprise a rigid single-piece core member that is molded from a plastic material. An elastomeric seal is commonly attached to the forward end of the plunger core for achieving a fluid-tight sliding seal between the plunger and the inside surface of the syringe body. An example of such a plunger is disclosed in U.S. Pat. No. 5,902,276. Other core members are of two-piece constructions that generally comprise a forward piece and a rearward piece that is dissimilar from the forward piece. Thus, such two-piece construction requires different molds to be employed for molding each core portion. This molding arrangement results in increased manufacturing costs because two different types of molds must be maintained and operated.

Regardless of the method employed to construct a syringe plunger, the plunger must be properly positioned within the syringe body such that it can be connected with the syringe drive member when the syringe is attached to the powered injector. If the plunger is cocked within the syringe body, it may be difficult to connect the drive member to the plunger. Furthermore, if the plunger is cocked within the syringe body, the seal between the plunger and the syringe body may be compromised which can lead to undesirable leakage between those components. As such, there is a need for a syringe plunger that is easy to manufacture and install and that does not have the problems associated with prior plunger designs.

Some injection procedures also involve the injection of a heated fluid into a patient. To accomplish such task, heater "blankets" have been developed that are designed to snap around the cylindrical syringe body to heat the fluid therein. In general, such heater blankets comprise a flexible resistance heater that is encapsulated in rubber material and is formed in a semi-circular shape for close fitting engagement with the syringe body. The heater blankets are attached, via cable, to an electrical power source. Because the heat is transferred through the syringe body, the efficiency of the heating process is dependent upon the close contact of the heater blanket to the syringe body. The heater blankets are commonly of split design that permits them to be snapped around the body of the syringe. Unfortunately, such construction requires each heater blanket to be formed to accommodate a specific size of syringe body. Therefore, larger heater blankets typically cannot effectively accommodate smaller syringes because they would loosely contact the syringe body and thus compromise heating efficiency. Accordingly, there is a need for an apparatus that can be used in connection with conventional heater blankets to enable one size of heater blanket to be used on a variety of different syringe body sizes.

SUMMARY OF THE INVENTION

In accordance with one form of the present invention, there is provided a syringe plunger that comprises a first core half that has first core attachment members and a second core half that is substantially identical to the first core half. The second core half has second core attachment members for complementary engagement with the first core attachment members to interconnect the first core half to the second core half. The plunger core may be provided with an anti-cocking flange that prevents the syringe from becoming axially misaligned within the syringe body which could compromise the seal between the plunger and the syringe body. An alignment flange may also be provided on the plunger which facilitates proper assembly of the plunger into the syringe.

The present invention may also comprise a syringe plunger having a rear attachment portion for engaging an injector drive member. In a preferred embodiment, the rear attachment portion may comprise a blade portion axially aligned on a central axis of the plunger, and an attachment member or button attached to the blade portion. The attachment button is preferably substantially perpendicular to the central axis of the plunger. Preferably the rear attachment portion of the plunger allows the plunger to be placed in a driven state or an undriven state at any position of the plunger within the syringe.

The present invention may also comprise a mounting member for removably affixing a syringe to an injector that contains a driven plunger rod. The mounting member may include a faceplate that has a forward face and syringe attachment members for cooperation with syringe retaining members on the rearward end of a syringe body to removably affix the syringe to the faceplate by axially inserting the rearward portion of the syringe body into an interface formed in the faceplate and rotating the syringe about a syringe axis that is perpendicular to the forward face. The faceplate may be pivotally attachable to the injector housing such that the faceplate is pivotable to an injection position wherein the interface is aligned with the drive rod in the injector. The faceplate may be equipped with a locking mechanism that automatically releasably retains the faceplate in the injection position when it is pivoted to that position.

The present invention may also comprise a locking mechanism for a syringe mounting plate that is pivotally attached to an injector housing and pivotable to an injection position. The locking mechanism may include a locking member on the injector and a retaining member affixed to the mounting plate such that it automatically releasably engages the locking member on the injector when the mounting plate is pivoted to the injection position. In one embodiment, the locking member comprises a pin and the retaining member comprises a spring clip. In another embodiment, the locking member comprises a locking pin and the retention member comprises a spring-biased ball detent.

The present invention may also include a retainer member for retaining a heater blanket in close contact with a syringe body. In one embodiment, the retainer member comprises a split sleeve with an internal diameter that is less than an external diameter of the syringe body.

It is a feature of the present invention to provide a means for mounting a front-loading syringe to a powered injector that is relatively inexpensive to manufacture and easy to install.

It is another feature of the present invention to provide a unique and novel plunger construction that is easier to manufacture than prior single and two-piece plunger designs.

It is yet another feature of the present invention to provide a plunger that is maintained in axial alignment with the syringe body to prevent leakage between the syringe and the plunger.

Yet another feature of the present invention is to provide a plunger that can be automatically installed in a syringe body in a predetermined orientation that facilitates engagement of the plunger with a plunger drive rod when the syringe is coupled to the injector.

It is still another feature of the present invention to provide an apparatus that enables a conventional syringe heater blanket to be used effectively on a variety of different syringes.

Accordingly, the present invention provides solutions to the shortcomings of prior syringe and powered injector systems. Those of ordinary skill in the art will readily appreciate, however, that these and other details, features and advantages will become further apparent as the following detailed description of the embodiments proceeds.

BRIEF DESCRIPTION OF THE DRAWINGS

In the accompanying Figures, there are shown present embodiments of the invention wherein like reference numerals are employed to designate like parts and wherein.

DETAILED DESCRIPTION OF THE EMBODIMENTS OF THE INVENTION

Figure 1:
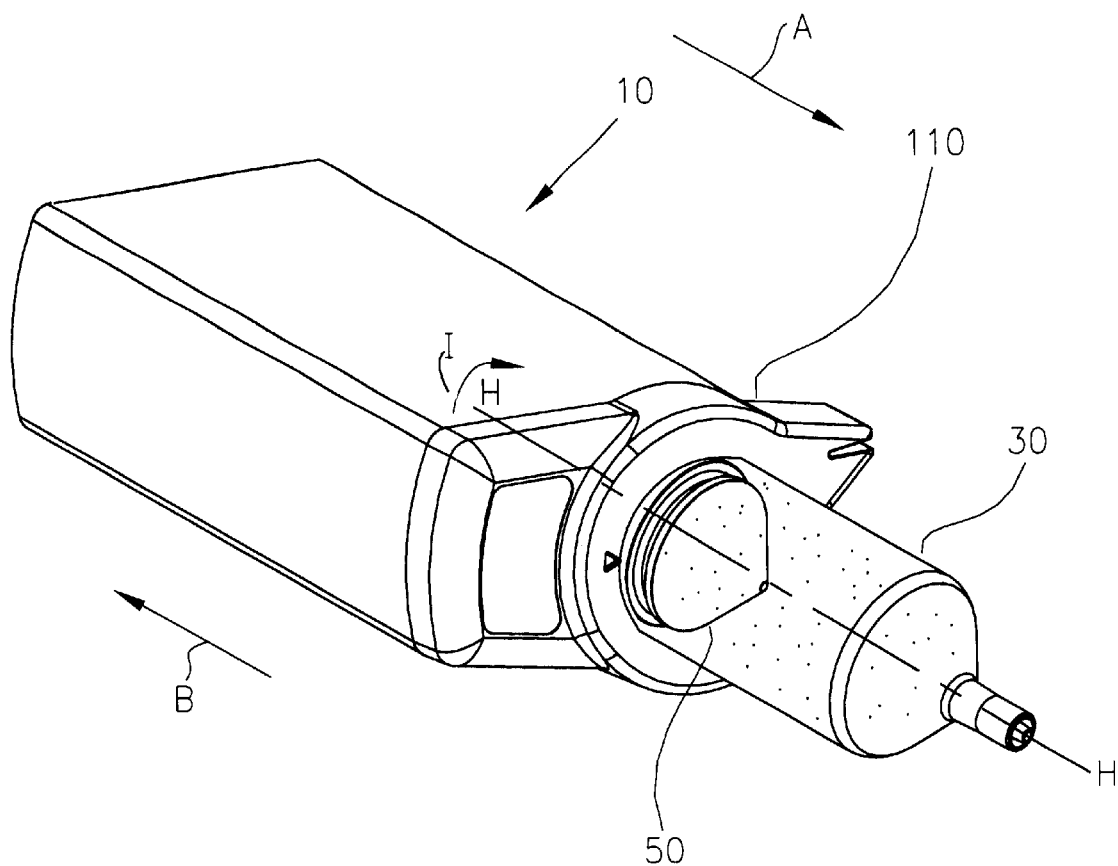
FIG. 1 is a perspective view of a mounting member of the present invention attaching a syringe to a powered injector.
Figure 2:
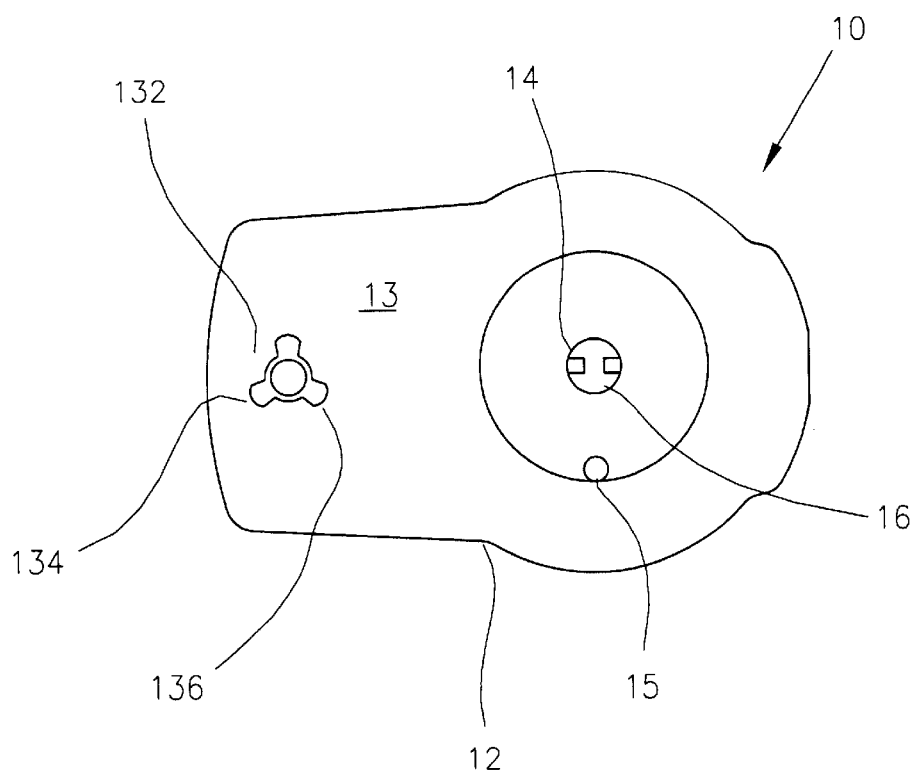
FIG. 2 is a front elevational view of the powered injector of FIG. 1 with the mounting member removed therefrom.
Figure 3:
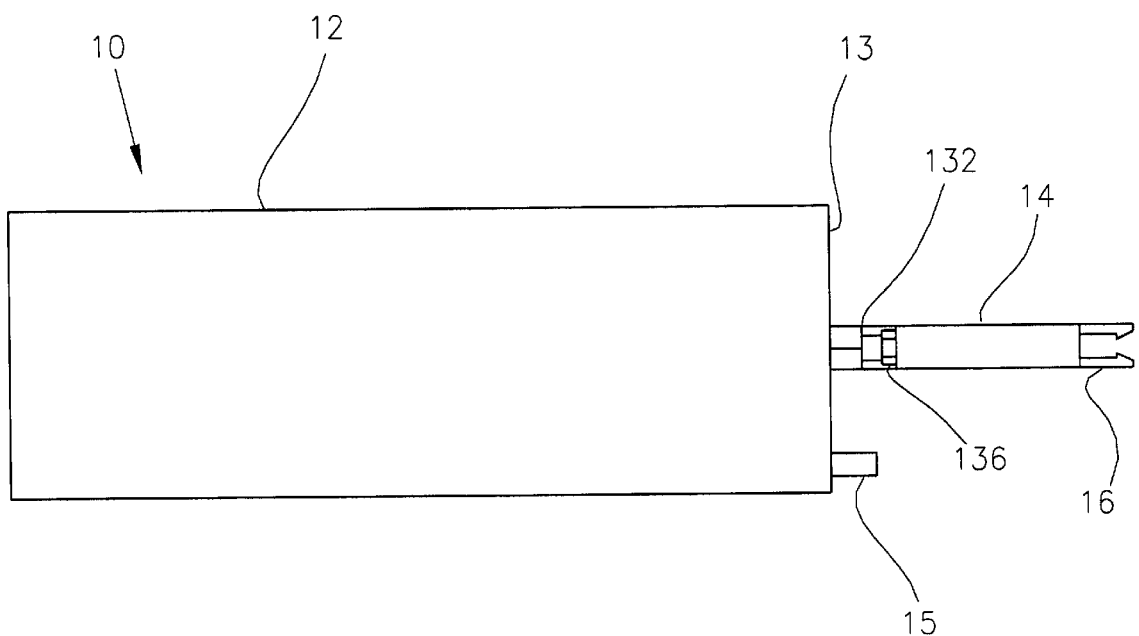
FIG. 3 is a side elevational view of the powered injector of FIG. 2, with the plunger drive member moved to an extended position.
Figure 4:
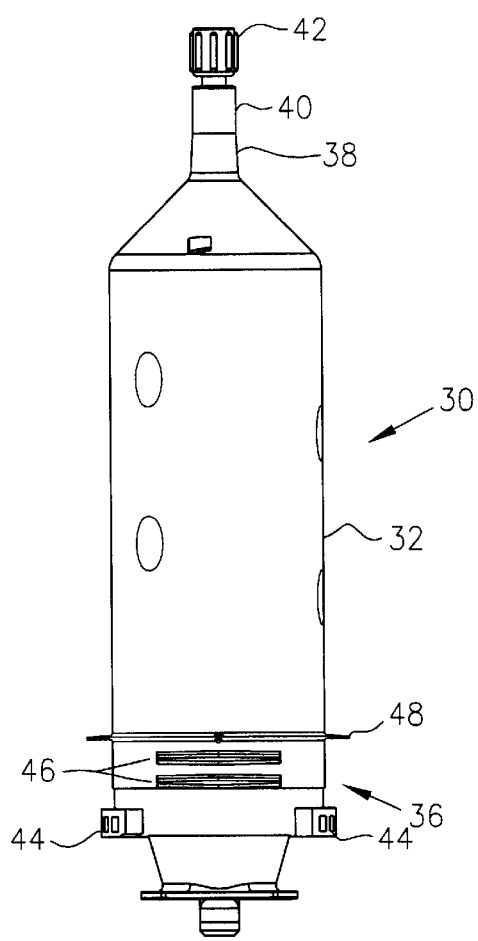
FIG. 4 is a side view of a syringe containing a plunger of the present invention.
Figure 5:
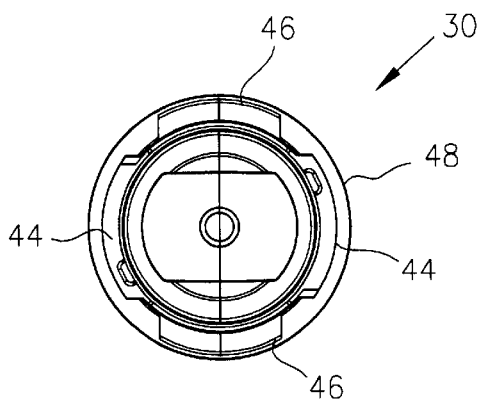
FIG. 5 is an end view of the syringe of FIG. 4.
Figure 6:
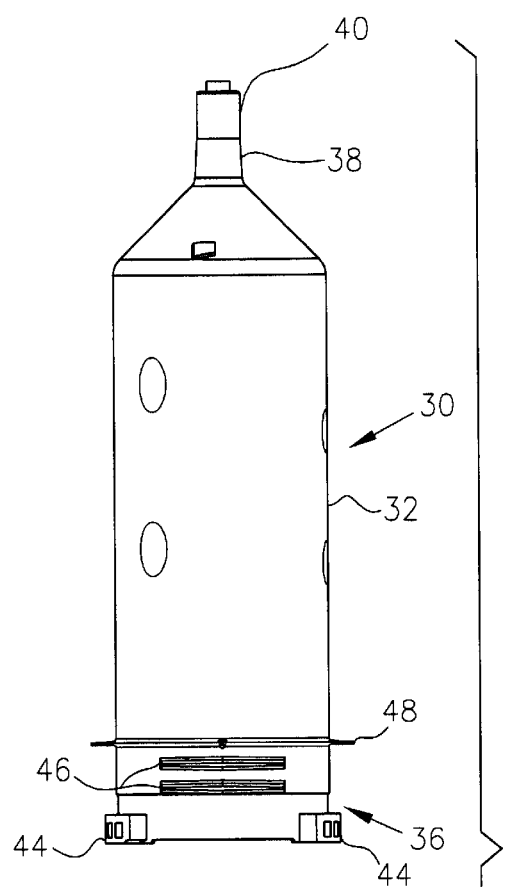
FIG. 6 is an exploded assembly view of the syringe of FIGS. 4 and 5.
Figure 6:
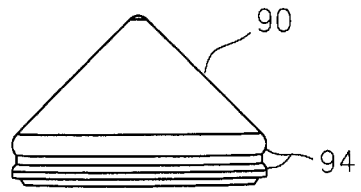
Figure 6:
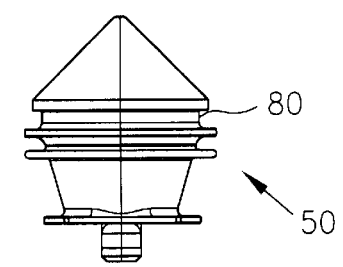

Referring now to the drawings for the purposes of illustrating the present preferred embodiments of the invention only and not for the purposes of limiting the same, FIG. 1 illustrates one embodiment of the mounting member 110 of the present invention attached to a commercially available powered injector 10. The construction and operation of such powered injectors are well known in the art and, therefore, their construction and operation will not be discussed in great detail herein beyond that which is necessary to understand the operation of the present invention. The reader will appreciate that the powered injector 10 includes a housing 12 that operates a power driven plunger drive member 14 that is extendable in the "A" direction and retractable in the "B" direction. A plunger attachment assembly 16 is provided at the end of the plunger drive member 14 for attachment to a syringe plunger. See FIGS. 2 and 3. The construction and operation of the plunger attachment assembly 16 will be described in further detail below.

As the present Detailed Description proceeds, those of ordinary skill in the art will appreciate that the mounting member 110 of the present invention may be used to operably attach a variety of syringe configurations to a powered injector 10. One type of syringe 30 that may be attached to the powered injector 10 by a mounting member 110 of the present invention is depicted in FIGS. 4–7. The syringe 30 includes a hollow cylindrical body 32 that has an interior surface 34. See FIG. 7. The cylindrical body 32 has a rearward portion 36 and a forward discharge portion 38. The forward discharge portion 38 may be formed with a screw threaded cylindrical connection portion 40 to facilitate attachment to a patient connector or fluid supply tubing 42 or to other appropriate port arrangements. The syringe 30 may be delivered to the customer as an "empty" syringe or as a "prefilled" syringe.

To facilitate attachment of the syringe 30 to the mounting member 110, this syringe embodiment is equipped with a first pair of attachment flanges 44 that extend around opposing portions of the syringe body 32. See FIG. 5. In this embodiment, the syringe 30 is also equipped with two additional pairs of spaced attachment fins 46 that are arranged at 90° with respect to the attachment flanges 44. Also, an annular drip flange or skirt 48 is formed around the outer perimeter of the syringe body. See U.S. Pat. No. 5,944,694, the contents of which are hereby incorporated by reference. Those of ordinary skill in the art will appreciate that the drip flange 48 serves to achieve a seal with a forward face 114 of the mounting member 110 to prevent the infiltration of fluid that might inadvertently drip and advance rearwardly along the syringe body 32 from entering the injector housing 12. Such syringe body configuration of the type described above is known in the art (see U.S. Pat. No. 5,383,858) and is commonly employed with front-loading powered injectors. Thus, the skilled artisan will appreciate that the syringe body 32 may be fabricated from, for example, polypropylene or other moldable plastics and polymers. However, it will be further appreciated that the syringe body may be fabricated from other suitable materials.

Figure 7:
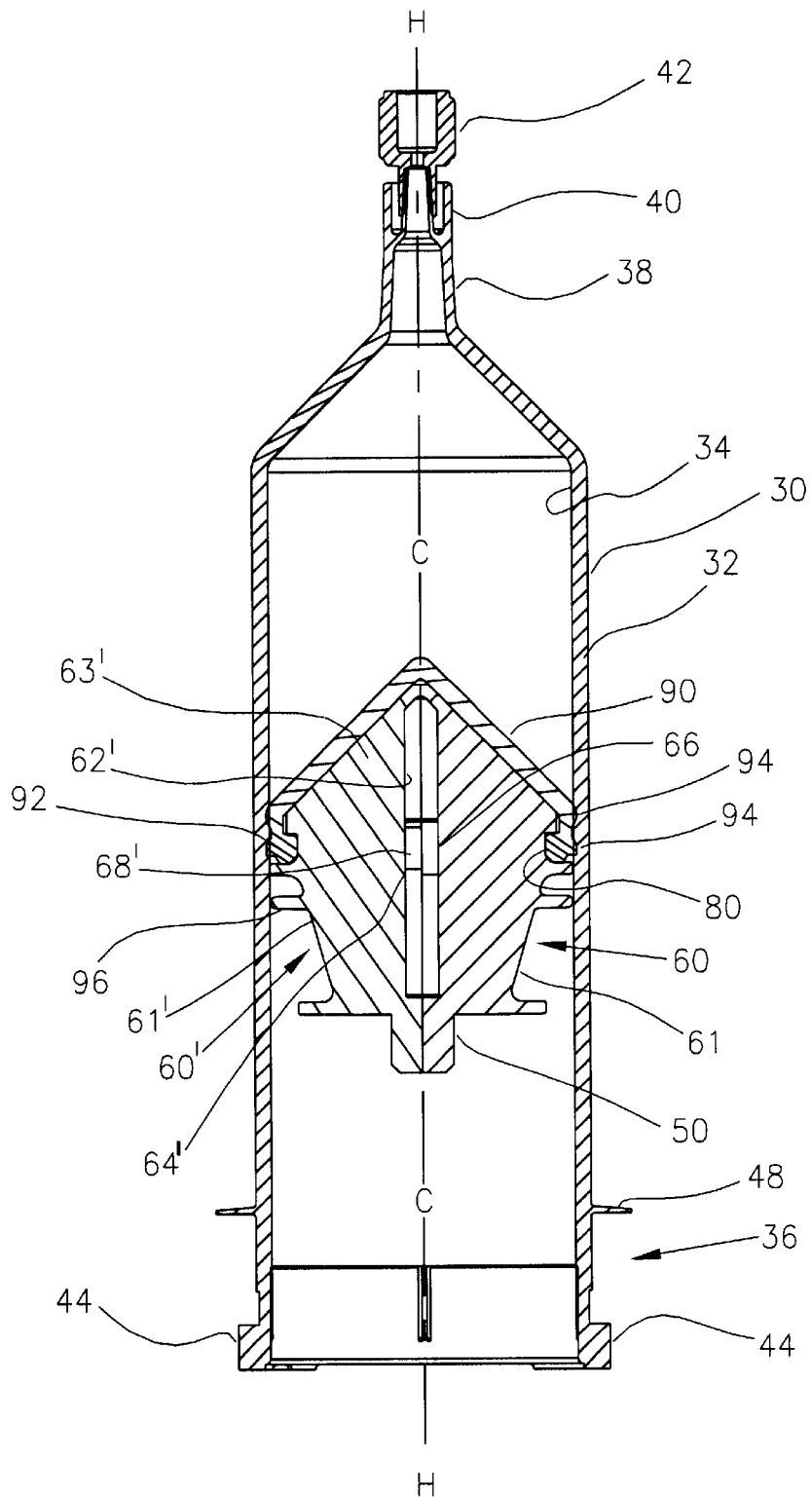
FIG. 7 is a cross-sectional view of a syringe containing a plunger of the present invention.
Figure 9:
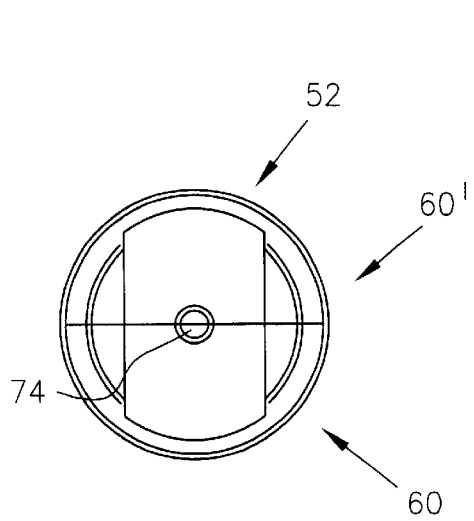
FIG. 9 is an end view of the plunger of FIG. 8.
Figure 8:
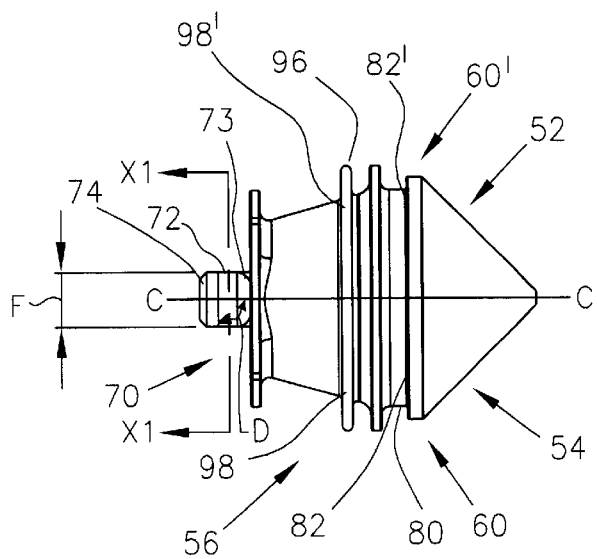
FIG. 8 is a side view of a plunger of the present invention.
Figure 11:
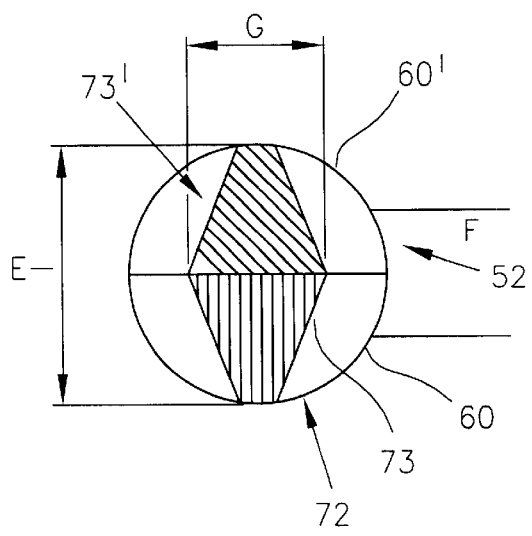
FIG. 11 is a cross-sectional view of the plunger of FIGS. 8–10 taken along line XI—XI in FIG. 8.
Figure 10:
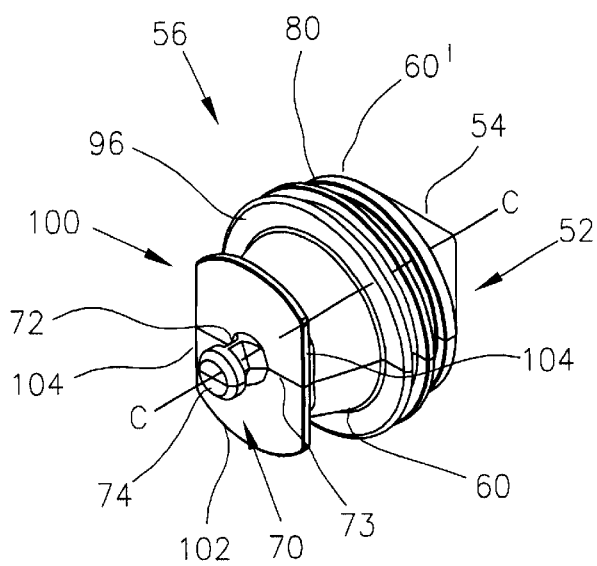
FIG. 10 is a perspective view of the plunger of FIGS. 8 and 9.

As can be seen in FIG. 7, a plunger member 50 is slidably supported within the syringe body 32. In one embodiment of the present invention, the plunger member 50 comprises a plunger core 52 that is molded from, for example, polycarbonate material. A seal or plunger cover 90 is also attached to the plunger core 52. More specifically and with reference to FIGS. 8–13, the plunger core 52 comprises a first plunger core half 60 and a second plunger core half 60' that is substantially identical in construction to the first plunger core half 60. As used herein, the term "substantially identical" means that the first and second core halves (60, 60') are molded from the same or similarly constructed molds and are of the same size, shape and composition. First plunger core half 60 will be described in detail herein, with it being understood that the second plunger core half 60' is substantially identical thereto. The first core half 60 has a first outer perimeter 61 and a first interior generally designated as 62. See FIG. 13. In this embodiment, a plurality of first support webs 63 is molded in the first interior 62 to provide support to the first outer perimeter 61. Those of ordinary skill in the art will appreciate that such configuration enables the first core half 60 to be molded from less material than a plunger that is molded with a solid core.

The first and second core halves (60, 60') may be molded by conventional molding techniques and processes. Those of ordinary skill in the art will readily appreciate that such manufacturing method eliminates the costs associated with fabricating and maintaining two different sets of molds. Moreover, the skilled artisan will readily appreciate that such molded construction results in faster mold cycle times when compared to the mold cycle times required to mold a solid single piece plunger which must be immersed in a cooling liquid to control the shrinkage of the plastic material during cooling. In addition, the split plunger design of the present invention allows for "coring out" of the inside of the core halves (i.e. the molding of cavities between the support webs) which facilitates better cooling and shrinkage control of the core halves during the molding process.

Figure 12:
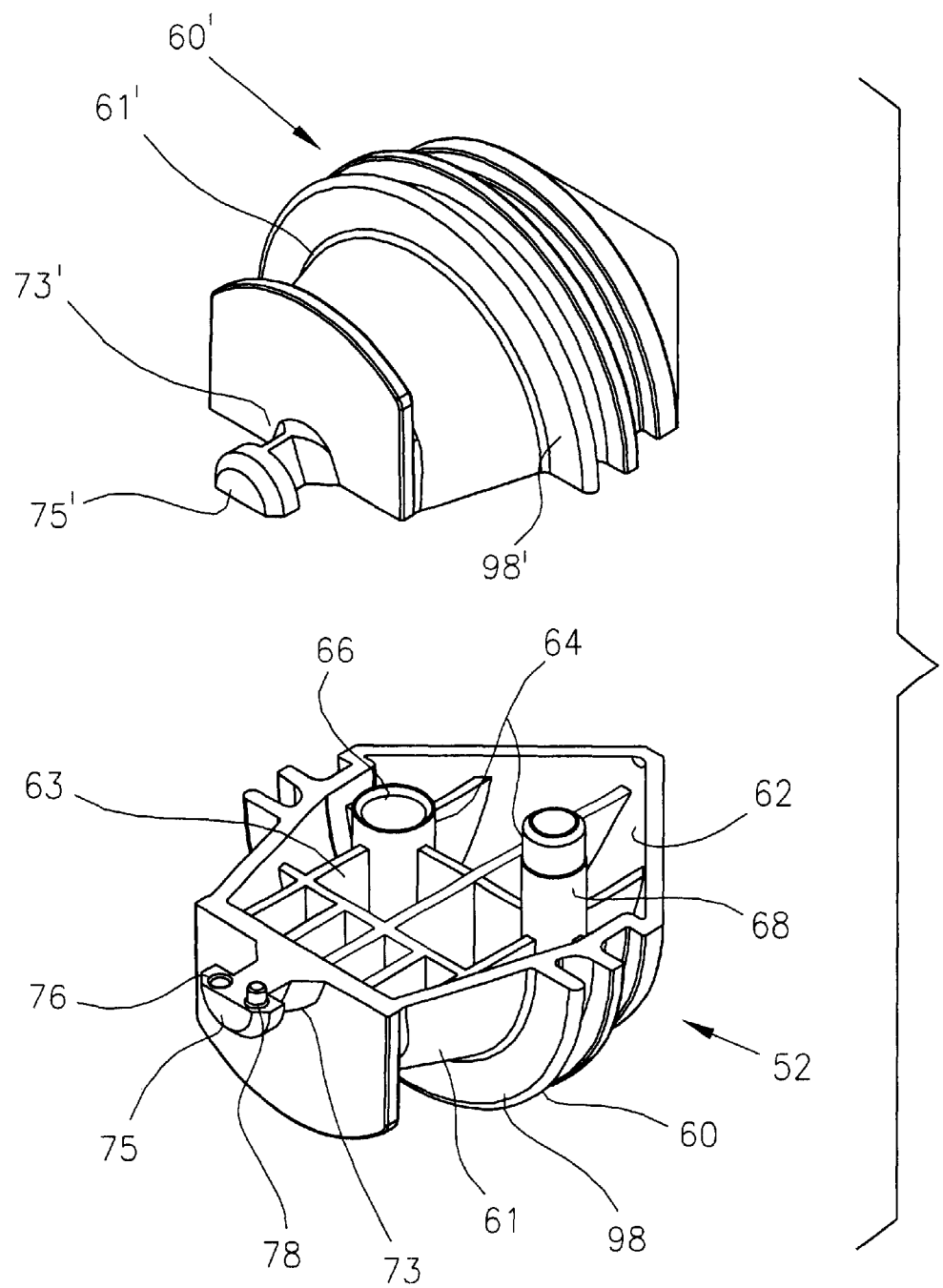
FIG. 12 is an exploded assembly view of the plunger of FIGS. 8–11.
Figure 13:
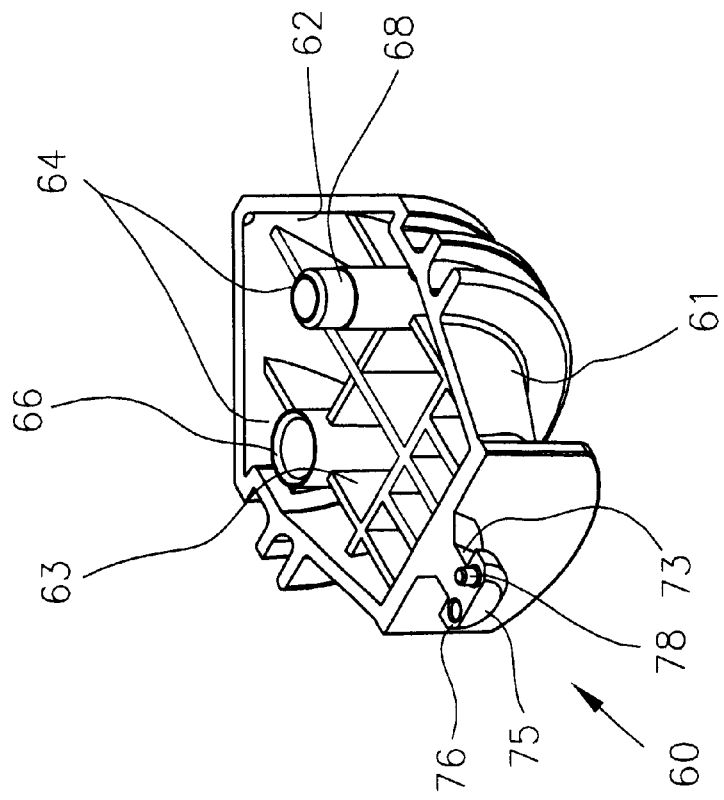
FIG. 13 is a perspective view of a first plunger core half and a second plunger core half of the present invention.
Figure 13:
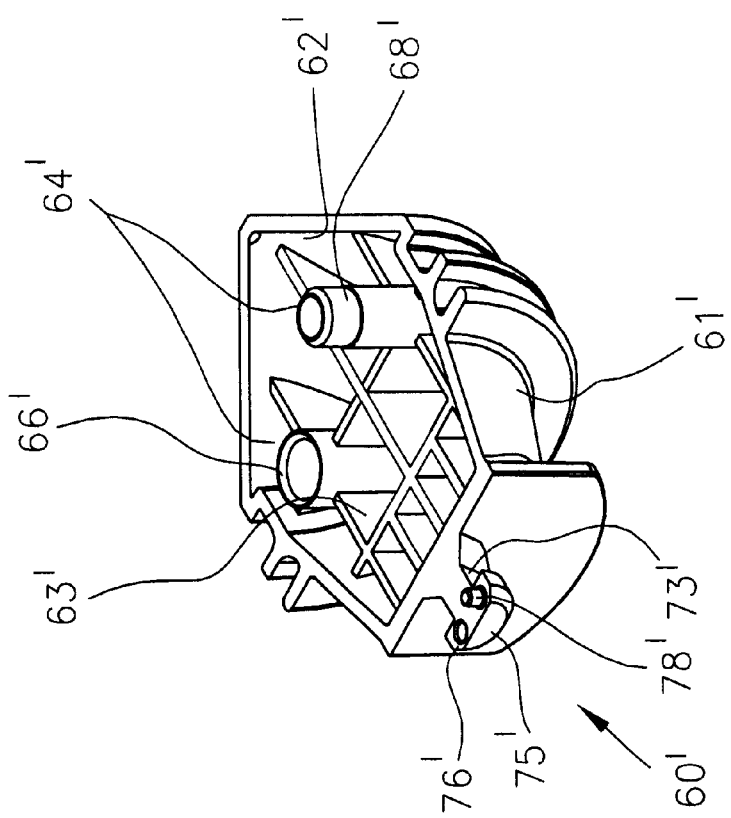

As can also be seen in FIGS. 12 and 13, a first core attachment means, generally designated as 64, is provided in the first interior cavity 62 of the first core half 60. In this embodiment, the first core attachment means 64 comprises a first socket 66 and a first attachment rod 68. Similarly, the second core half 60' has a second outer perimeter 61' and a second interior 62'. A second core attachment means, generally designated as 64', is provided in the second interior cavity of the second core half 60'. In this embodiment, the second core attachment means 64' includes a second socket 66' sized to frictionally receive and retain a portion of the first attachment rod 68 therein and a second attachment rod 64', a portion of which is sized to be frictionally received in the first socket 66. The skilled artisan will appreciate that when the portion of the first attachment rod 64 is inserted into the second socket 66' and a portion of the second attachment rod 64' is inserted into the first socket 66, the first and second core halves (60, 60') are retained together to form the plunger core 52.

As can also be seen in FIGS. 7–10, when assembled, the plunger core 52 includes a conical shaped forward portion 54, a central portion 56 and a rear plunger attachment portion 70 that are aligned along a central axis C—C. In this embodiment, the rear plunger attachment portion 70 comprises a blade portion 72 that is axially aligned on the central axis C—C and an attachment button 74 that is attached to the blade portion 72 such that it is substantially perpendicular to the central axis C—C (i.e., angle "D" is approximately 90°). See FIG. 8. Blade portion 72 is formed from a first blade half 73 on the first core half 60 and a second blade half 73' on the second core half 60'. Similarly, the attachment button 74 is formed from a first attachment button half 75 on the first core half 60 and a second attachment button half 75' on the second core half 60'. To further facilitate attachment of the first core half 60 to the second core half 60', the first attachment button half 75 may be provided with a first button socket 76 and a first button rod 78. Similarly, the second button half 75' may be provided with a second button socket 76', sized to frictionally receive the first button rod 78 therein and a second rod 78' that is sized to be frictionally received in the first button socket 76. Thus, in this embodiment, the first and second core halves (60, 60') are retained together by frictional engagement between the above mentioned attachment components. It will be appreciated however, that the first and second core halves (60, 60') could be retained together by other fastening means such as adhesive, mechanical fasteners, snap fits, etc.

Also in this embodiment, the blade portion 72 of the plunger core 52 has a hexagonal cross-sectional shape that has a height "E" that is equal to the diameter "F" of the attachment button and a width "G" that is less than the height "E". See FIGS. 8 and 11. As will become further apparent as the present Detailed Description proceeds, such cross-sectional shape serves to facilitate easy attachment of the plunger 50 to the plunger attachment assembly 16 on the plunger drive member 14. It is conceivable, however, that the plunger blade portion 72 may have other cross-sectional shapes such as, for example, a shape in the form of a tetragon, etc. Similarly, the attachment button 74 in this embodiment is substantially round when viewed from the end of the plunger 50. However, the attachment button 74 could also conceivably be provided in other shapes that are conducive for releasable attachment to a plunger drive member 14 of a particular powered injector.

The assembled plunger core 52 may also be provided with an annular groove 80 that is adapted to receive an inwardly extending retaining flange 92 of the seal or plunger cover 90 when it is received on the forward conical portion 54 of the plunger core 52. In this embodiment, the seal member 90 is formed from an elastomeric material such as polyisoprene (e.g., synthetic rubber) or the like and is retained on the plunger core 52 by virtue of the receipt of the retaining flange 92 in the annular groove 80 in the plunger core 52. The annular groove 80 is formed by a first semi-annular groove 82 in the perimeter of the first core half 60 and a second annular groove 82' in the second perimeter of the second core half 60'. The outer circumference of the seal 90 is also provided with a pair of sealing ribs 94 for establishing a seal between the plunger 50 and the inside surface 34 of the syringe body 32.

Also in this embodiment, the plunger core 52 is provided with an anti-cocking flange 96 for maintaining the plunger 50 in coaxial alignment with the central axis H—H of the syringe body 32. See FIG. 7. Such arrangement maintains the sealing ribs 94 in sealing contact with the inside surface 34 of the syringe body 32. The anti-cocking flange 96 comprises an annular ring that extends around the perimeter of the plunger core 52 and is formed from a first anti-cocking flange segment 98 on the first core half 60 and a second anti-cocking flange segment 98' on the second core half 60'. The anti-cocking flange 96 may be sized such that it does not contact the interior surface 34 of the syringe body 32. For example, for a syringe body that has an internal diameter of 1.844 inches (±0.005"), the outer diameter of an anti-cocking flange may be, for example, 1.834 inches (±0.005"). However, other sizes of anti-cocking rings could also be successfully employed. Also, as can be seen in FIG. 7, in this embodiment, the outer perimeter 97 of the anti-cocking flange 96 is rounded such that should the anti-cocking flange 96 contact the interior surface 34 of the syringe body 32, the likelihood of the anti-cocking flange scraping and flaking off portions of the syringe body into the interior is minimized.

Various methods have been devised for inserting a plunger into a syringe to complete the syringe assembly. For example, in some assembly operations, specially made "pick and place" machines have been employed to insert the open end of a syringe body onto a plunger that is supported on a moving conveyor. The manner in which the syringe is attached to an injector and the manner in which the plunger is attached to the plunger drive, may dictate that the plunger be inserted into the syringe body in a specific orientation. In such applications, failure to properly orient the plunger within the syringe body may prevent the plunger from being attachable to the plunger drive after the syringe has been attached to the injector. Thus, another feature of the present invention is to provide an alignment member or flange 100 on the plunger core 52 that is sized to be received in a "complementary shaped" aperture in an assembly fixture 200. As used herein, the phrase "complementary shaped" means an aperture or hole shaped with respect to the shape of an alignment flange on a plunger core such that the alignment flange is supported in a desired orientation when the alignment flange is received therein.

Figure 14:
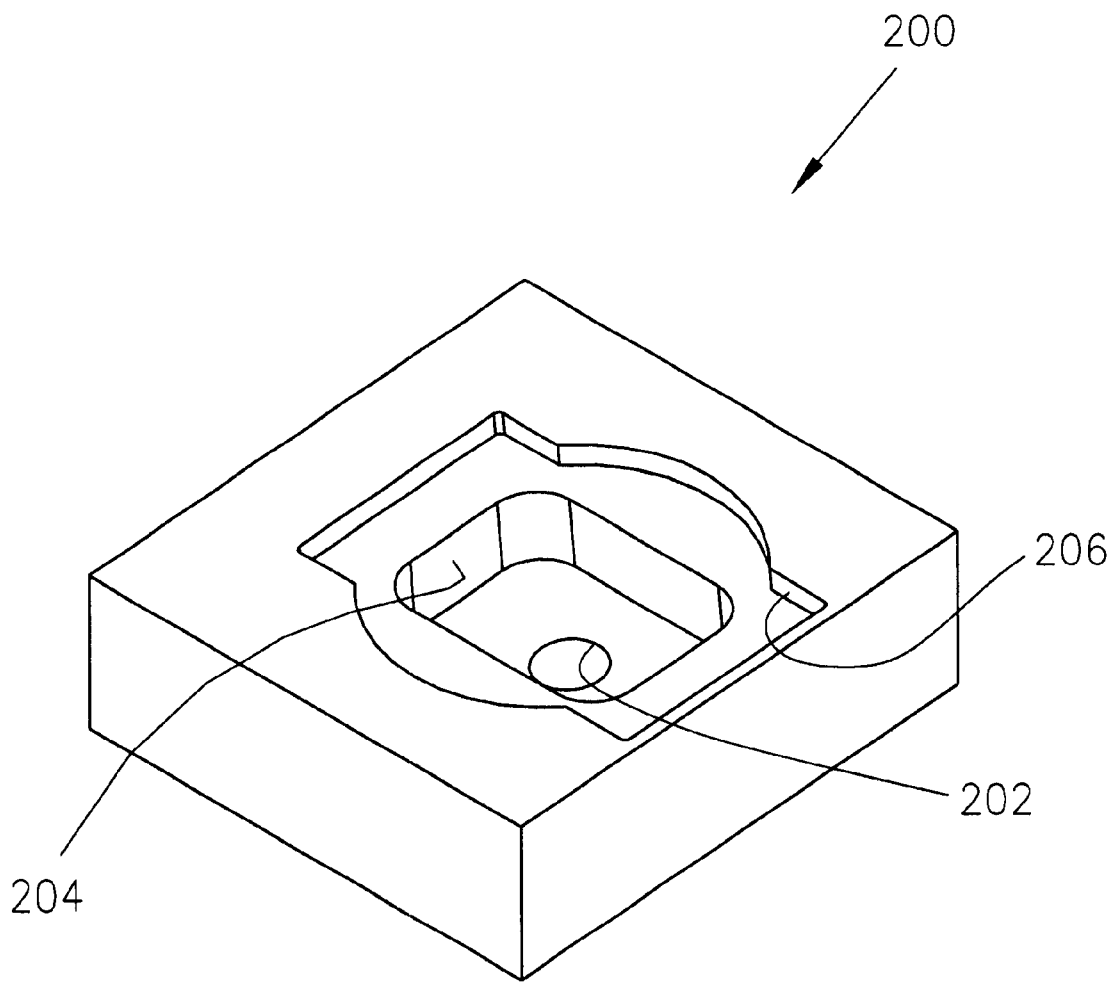
FIG. 14 is a perspective view of an assembly fixture.
Figure 15:
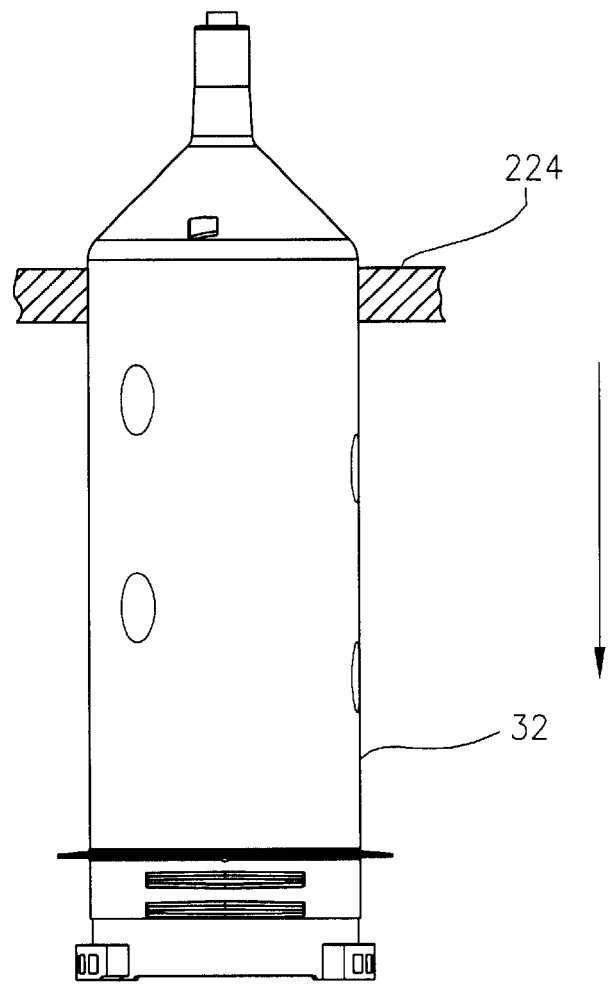
FIG. 15 is an exploded assembly view showing a plunger that is received in an assembly fixture positioned relative to a syringe prior to assembly with the syringe.
Figure 15:
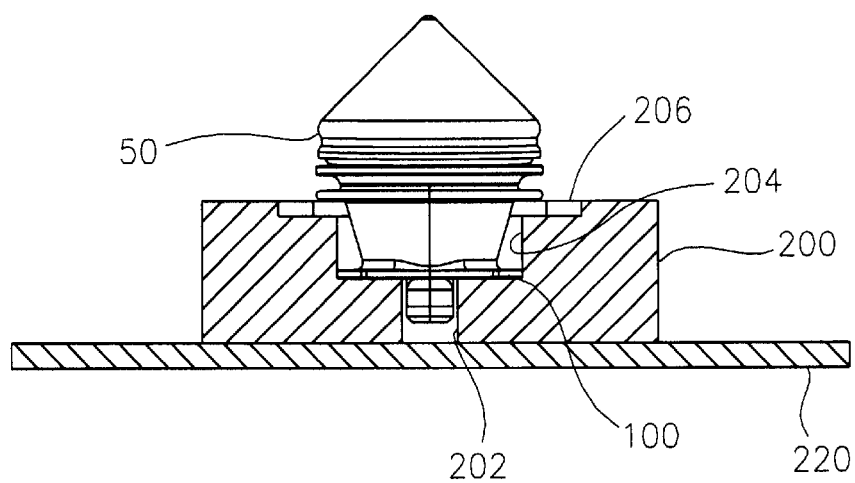
Figure 16:
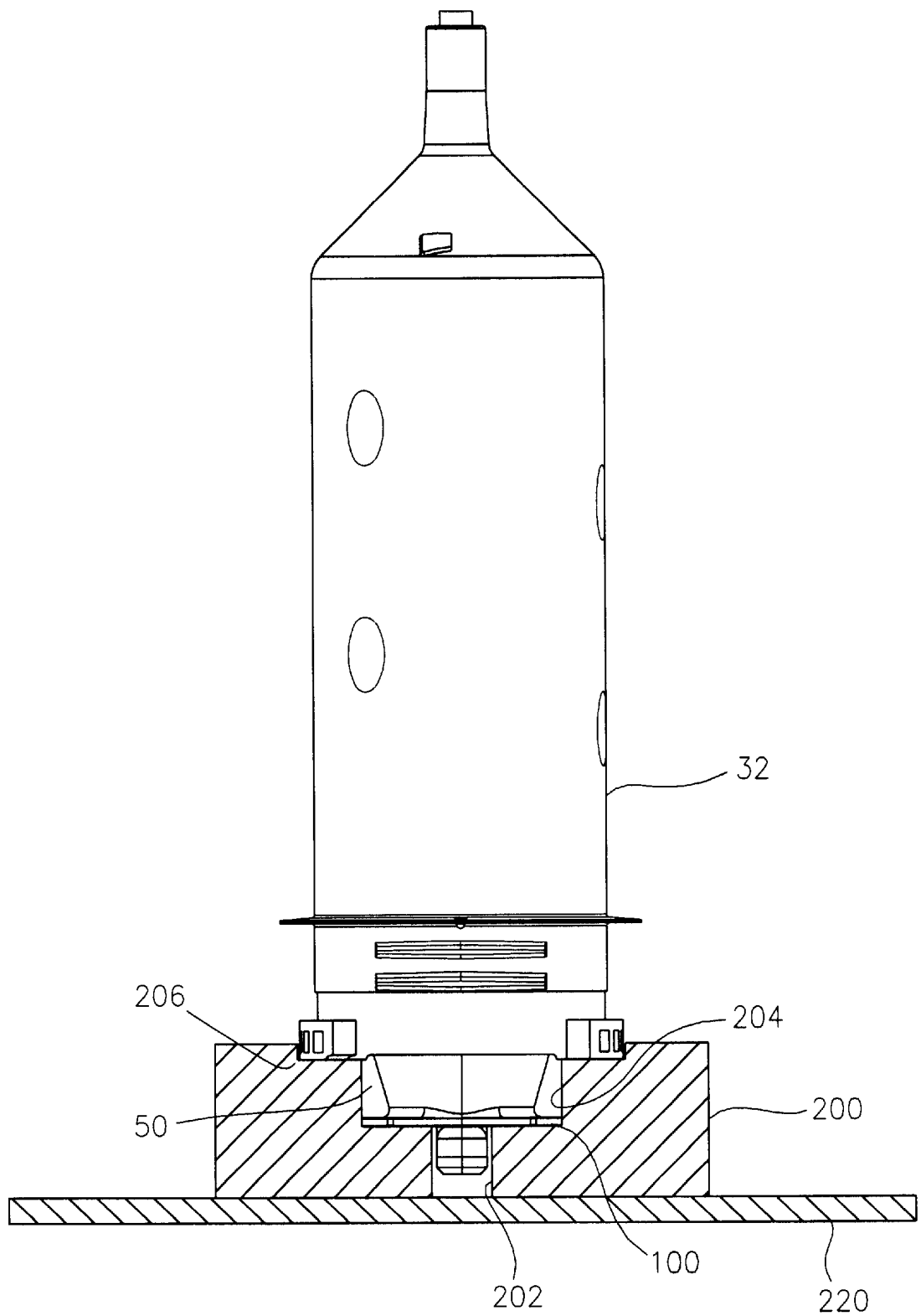
FIG. 16 is an assembly view showing the syringe inserted onto the plunger of FIG. 15.

One type of assembly fixture 200 that may be employed to properly orient a plunger 50 for assembly into a syringe is shown in FIG. 14. The assembly fixture 200 may be fabricated from a variety of materials such as aluminum, steel, polymers, etc. and supported on a conveyor belt 220. See FIGS. 15 and 16. In this particular embodiment, the assembly fixture 200 includes a first bore 202 that is sized to receive the attachment button 74 of a plunger 50 therein. A second aperture 204 is provided in the fixture and is complementary shaped with respect to the alignment flange 100 on the plunger. In this embodiment, the plunger core 52 is provided with an alignment flange 100 that has two arcuate ends (102, 102') and two flat sides 104 and is sized to be received within the second aperture 204 in assembly fixture 200. Aperture 204 is shaped such that when the alignment flange 100 is inserted into aperture 204, the plunger 50 is oriented in a desired position for assembly with a corresponding syringe body 32. A third aperture 206 is provided in the assembly fixture 200 which is complementary-shaped with respect to the open end of a syringe body 32.

The automated assembly of a plunger 50 and a syringe body 32 may be accomplished in the following manner. The plungers 50 may be placed in a vibratory bowl (not shown) or other type of orientation device that orients the plungers 50 in a desired orientation for introduction into corresponding assembly fixtures 200 that are supported on a conveyor belt 220. Each plunger 50 is so oriented such that the alignment flange 100 of a plunger 50 is oriented to fall into the complementary shaped second aperture 204 in the assembly fixture 200. See FIG. 15. After the plunger 50 is properly oriented in the assembly fixture 200, the conveyor 220 moves the assembly fixture 200 to a station wherein a pick and place machine 224 forces a pre-oriented syringe body 32 over the plunger 50 to complete the assembly. See FIG. 16.

Those of ordinary skill in the art will appreciate that the alignment flanges 100 and the complementary-shaped second apertures 204 in the assembly fixtures 200 may be provided in a myriad of other shapes. For example, an alignment flange 100 may have an oval, triangular, or other non-circular shapes and the second aperture 204 in the assembly fixture may be so shaped relative to the alignment flange 100, such that the alignment flange 100, when received therein, is oriented in a desired position for assembly. As the present Detailed Description proceeds, the reader will appreciate that such arrangement serves to ensure that the plunger 50 is properly oriented within the syringe body 32 such that when the syringe 30 is coupled to the injector, the attachment button 74 is properly oriented to facilitate coupling with the plunger drive rod 14 housed within the injector 10.

Figures 17, 18:
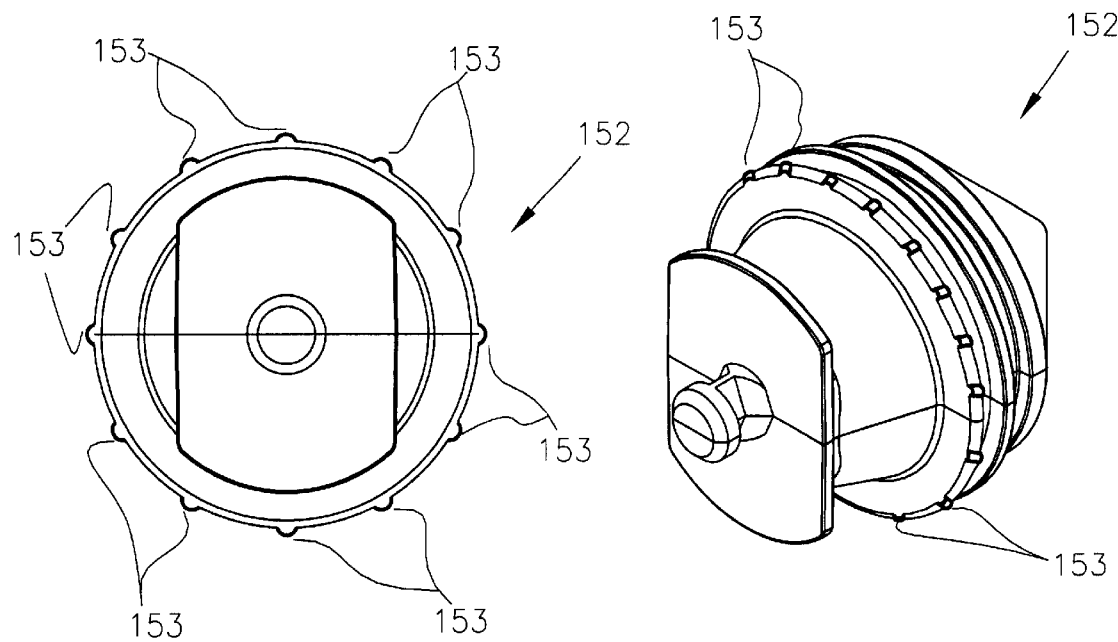
FIG. 17 is an end view of another plunger core of the present invention.
FIG. 18 is a perspective view of the plunger core of FIG. 17.
Figures 19, 20:
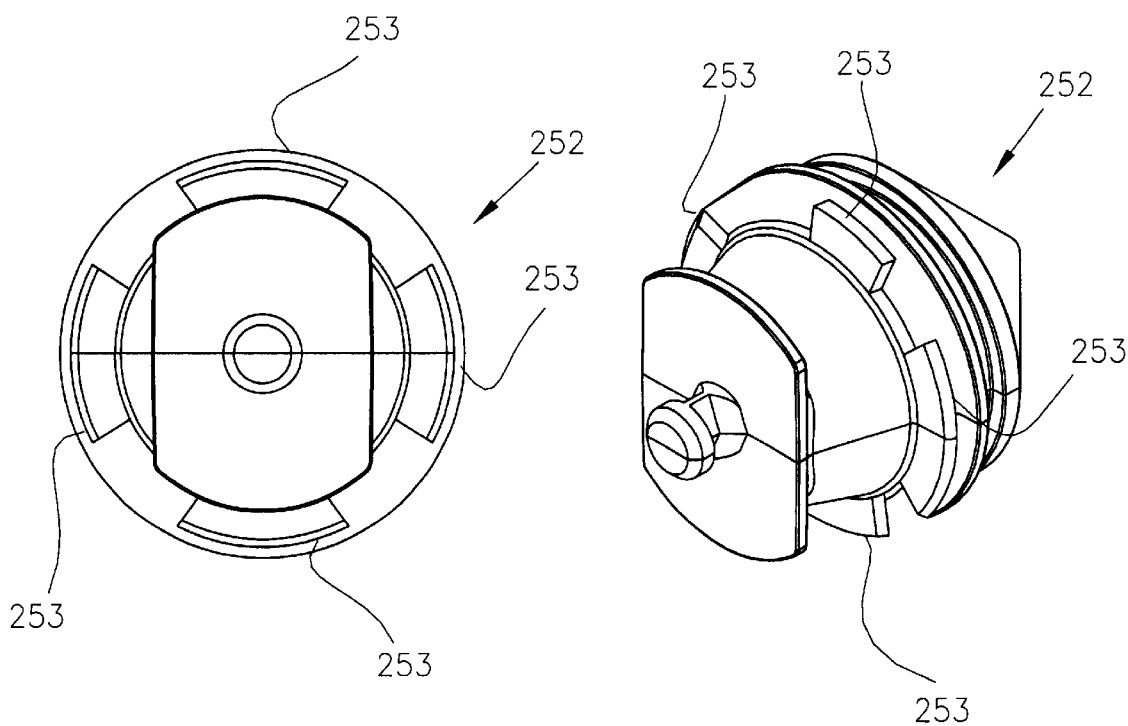
FIG. 19 is an end view of another plunger core of the present invention.
FIG. 20 is a perspective view of the plunger core of FIG. 19.
Figure 22:
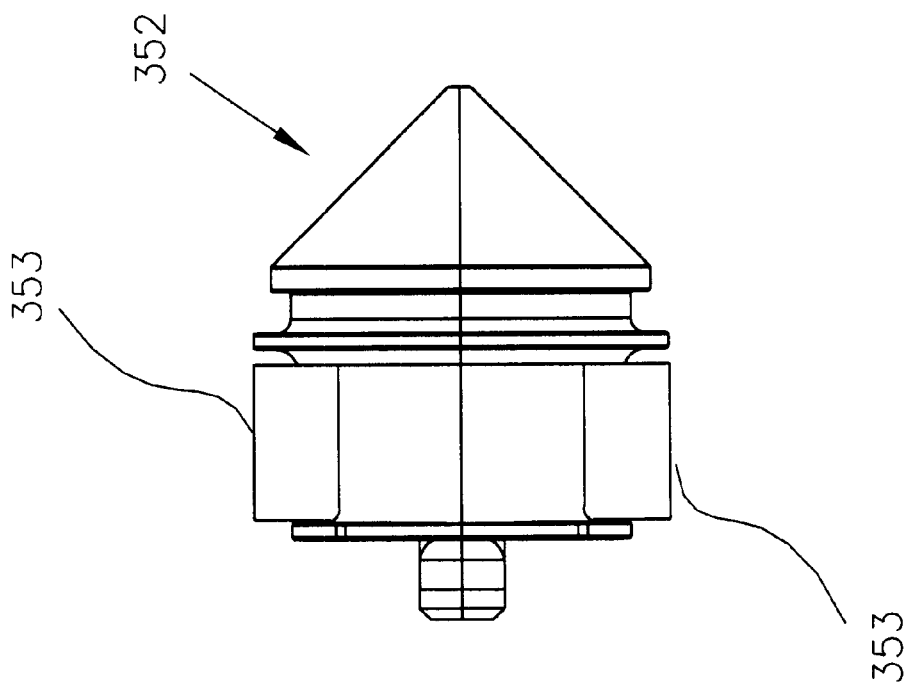
FIG. 22 is a side elevational view of the plunger core of FIG. 21.
Figure 21:
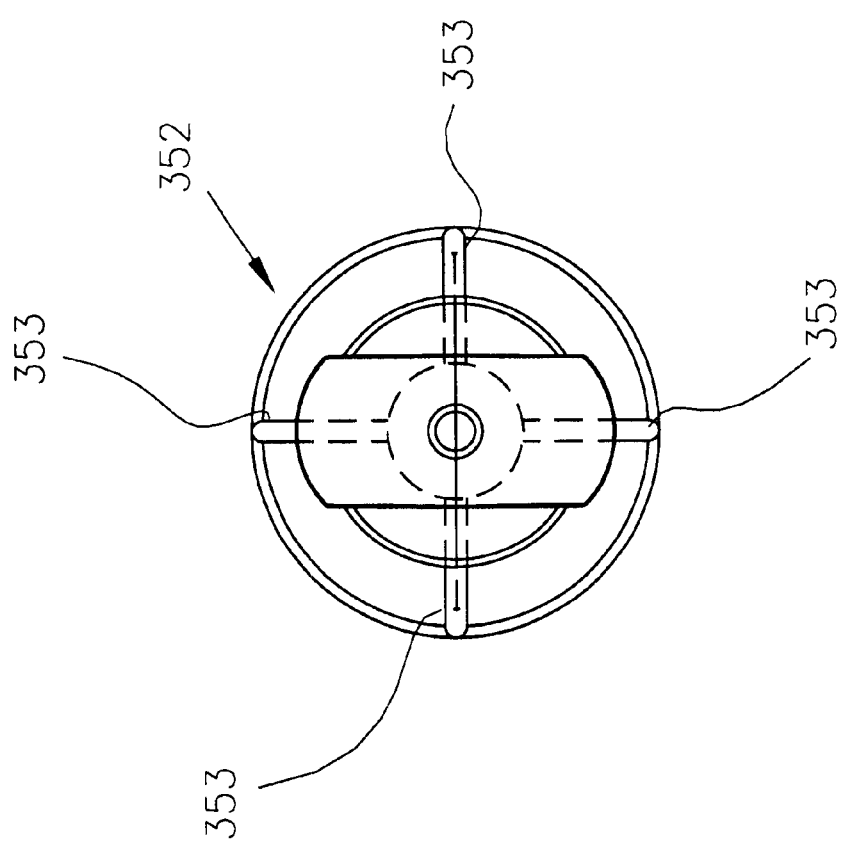
FIG. 21 is an end view of another plunger core of the present invention.

FIGS. 17 and 18 depict a plunger core 152 that is otherwise identical in construction and design as the plunger core 52 discussed above, except that the anti-cocking flange has a plurality of dimples 153 molded on its outer perimeter to achieve close-fitting alignment between the plunger core 152 and the syringe body 32. FIGS. 19 and 20 depict a plunger core 252 that is otherwise identical in construction and design as the plunger core 52 described above, except that the anti-cocking flange is formed from a plurality of segments 253. FIGS. 21 and 22 depict a plunger core 352 that is otherwise identical in construction and design as the plunger core 52 described above, except that it is provided with a plurality of axially extending anti-cocking flange segments 353. The reader will appreciate that, if so desired, all of the embodiments depicted in FIGS. 17–22 are formed by interconnecting two identical core halves.

Figure 24:
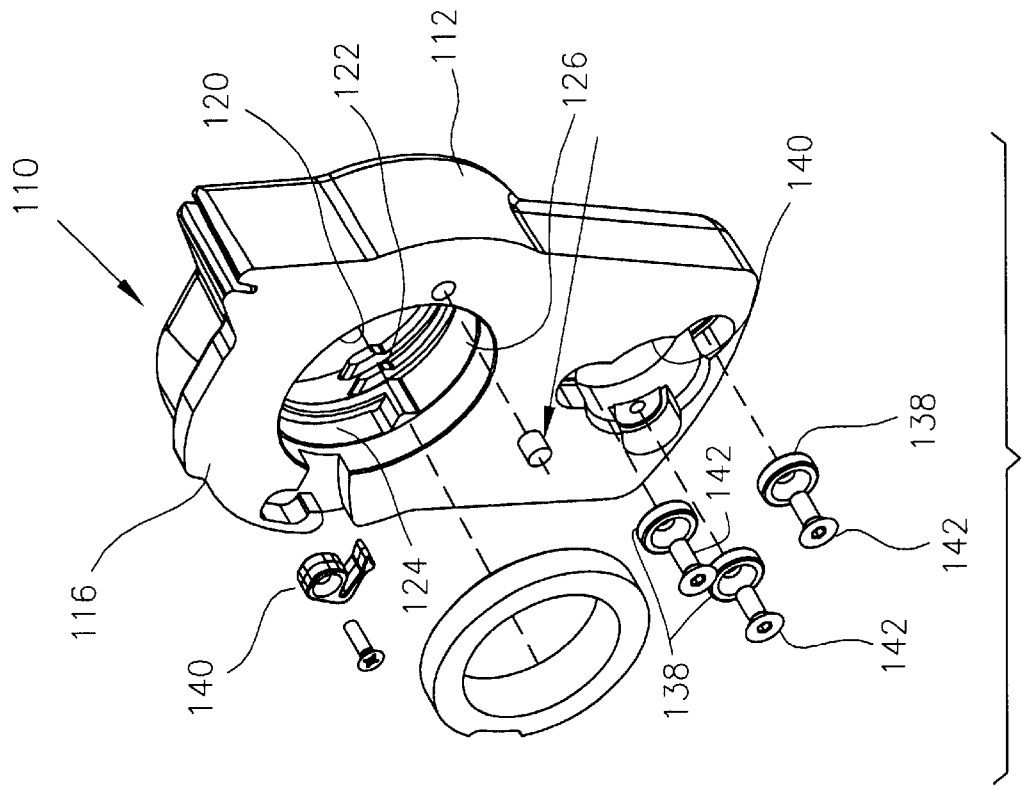
FIG. 24 is an exploded assembly view of the faceplate of FIG. 23.
Figure 23:
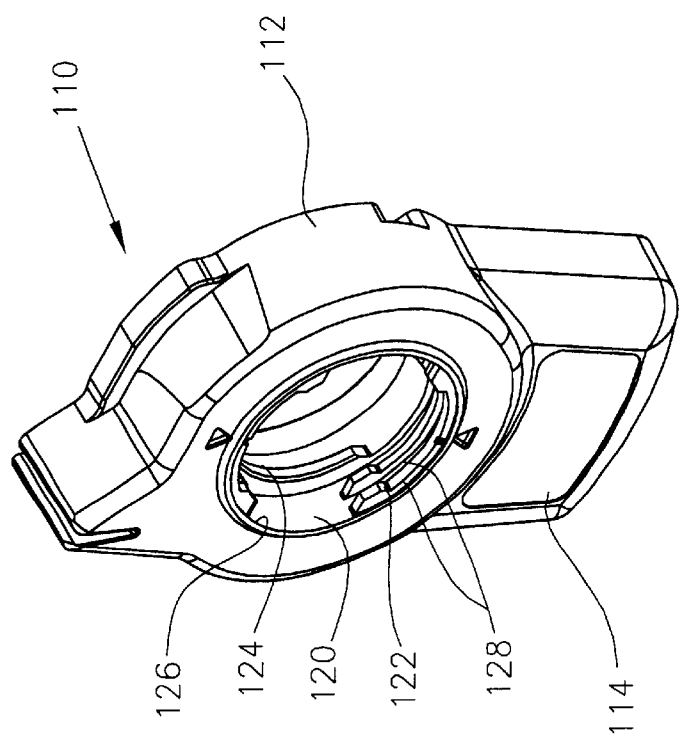
FIG. 23 is a perspective view of a faceplate of the present invention.
Figure 25:
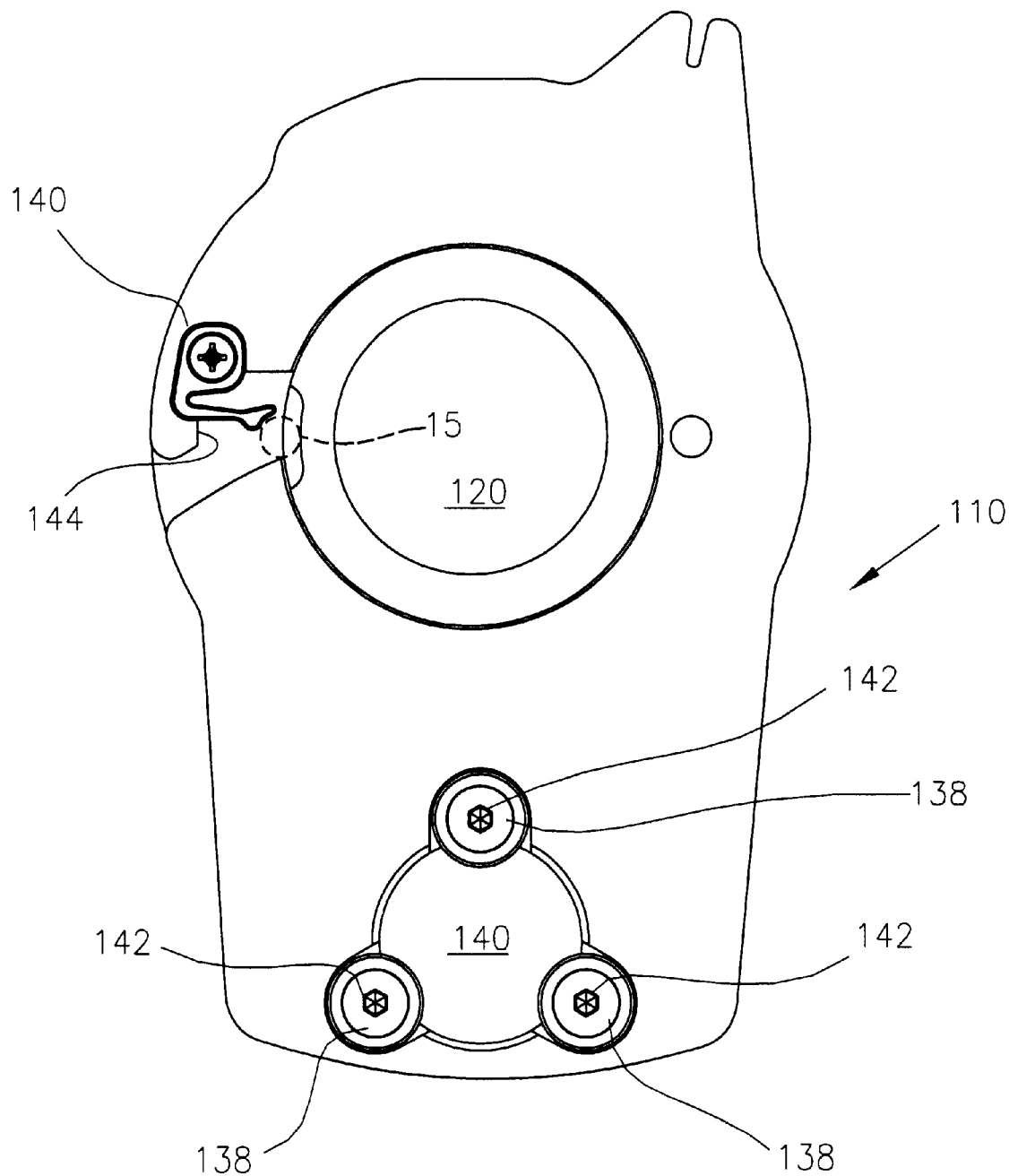
FIG. 25 is a rear view of the faceplate of FIGS. 23 and 24.

As discussed above, the mounting member 110 of the present invention is used to operably connect a front-loading syringe of the type described above or other front-loading syringe configuration to a powered injector 10. A mounting member 110 of the present invention is depicted in FIGS. 23–25. As can be seen in those Figures, this embodiment of the mounting member 110 comprises a faceplate 112 that has a forward face 114 and a rearward face 116. Faceplate 112 may be fabricated or molded from, for example, aluminum, or other suitable polymeric material such as Delrin and have a shape that complements the cross-sectional shape of the powered injector housing 12. However, the reader will appreciate that other faceplate shapes and sizes may be successfully employed.

The faceplate 112 has an interface formed therein for receiving the rearward end 36 of a syringe 30. The interface 120 includes a pair of slots 122 through which the pair of first attachment flanges 44 formed on the rearward end 36 of the syringe body 32 may pass. A pair of primary retention flanges 124 are formed around opposing portions of the interface 120 for engagement with the first attachment flanges 44 on the syringe body 32. A second pair of opposing slots 126 is provided in the faceplate 110 through which attachment fins 46 on the syringe body 32 may pass when the first attachment flanges 44 are inserted through slots 122. Secondary retaining flanges 120 are formed around other opposing portions of the interface 120 for engagement with the attachment fins 46. Thus, to attach a syringe 30 to the faceplate 110, the rearward end 36 of the syringe is aligned with the interface 120 along a syringe axis H—H that is substantially perpendicular to the forward face 114 of the face plate 112 such that the first attachment flanges 44 are aligned with the first slots 122 and the attachment fins 46 are aligned with the slots 126. The syringe body 32 is then inserted into the interface 120 and rotated 90° to bring the first attachment flanges 44 into engagement with the primary retention flanges 124 and the attachment fins 46 are brought into engagement with the secondary retaining flanges 128. Those of ordinary skill in the art will appreciate that similar syringe attachment flange arrangements are disclosed in U.S. Pat. No. 6,090,064, the disclosure of which is herein incorporated by reference. It will be further appreciated, however, that other "front loading" attachment arrangements may be employed for removably attaching the syringe to the faceplate 112.

The faceplate 112 may be pivotally attached to the forward end 13 of the injector housing 12 by a pivot pin assembly 130. More particularly and with reference to FIGS. 2, 3, 24, and 25, a pivot pin 132 is provided on the forward end 13 of the injector housing 12 such that it protrudes therefrom. Pivot pin 132 is provided with a retaining flange 134 that has a series of notches 136 therein that are adapted to receive portions of retainer washers 138 attached to the faceplate 112. As can be seen in FIG. 25, retainer washers 138 are spaced around an attachment cavity 140 sized to receive the retaining flange 134 and are retained in position by corresponding screws 142. To attach the faceplate 112 to the injector housing 12, the faceplate 112 is aligned with the retaining flange 134 such that the retainer washers 138 are aligned with the notches 136. The faceplate 112 is then advanced towards the injector housing 12 such that the retaining flange 134 is received in the attachment cavity 140. The faceplate 112 is then rotated in the "I" direction (FIG. 1) and the faceplate 112 is retained on the pivot pin 132 by virtue of engagement between the retainer washers 138 and the retaining flange 134.

Figure 26:
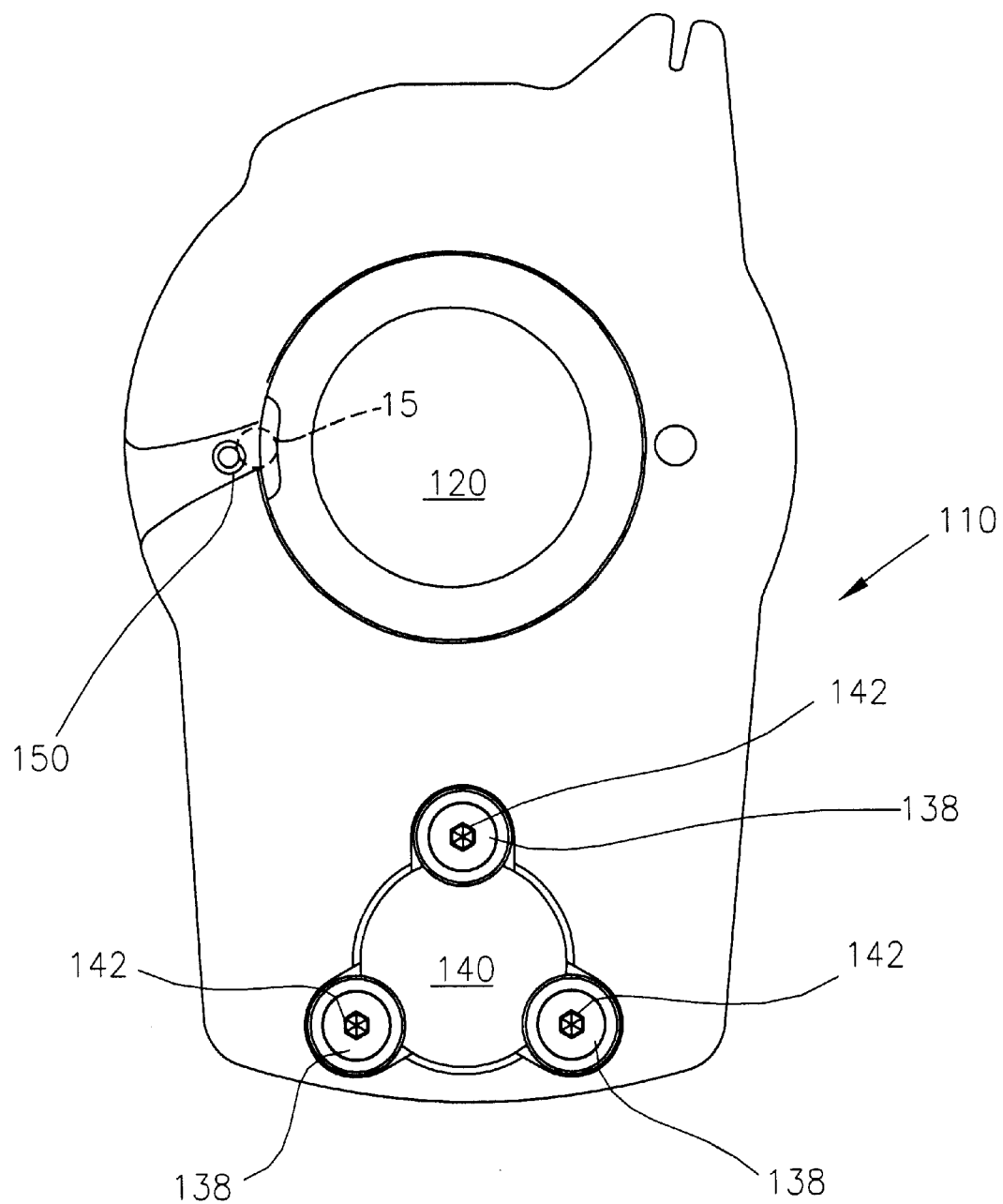
FIG. 26 is a rear view of another faceplate of the present invention.

The faceplate 112 is pivotable between a position wherein it is initially inserted onto the pivot pin 132 and an injection position wherein the drive member 14 is free to protrude into the interface 120 in the faceplate 112 and ultimately into the syringe 30 attached thereto. FIG. 1 illustrates the faceplate 112 in an injection position. In this embodiment, the faceplate 110 is releasably retained in the injection position by a retaining member in the form of a spring clip 140 that is sized to releasably engage a locking member or pin 142 that protrudes from the forward end 13 of the injector housing 12. Spring clip 140 may be received in a spring clip cavity 144 provided on the rear face of the faceplate and attached thereto by a screw or other suitable fastener. In one embodiment, the spring clip is fabricated from molded plastic or polycarbonate. However, the spring clip 140 may be fabricated from other suitable materials such as metal and the like and have other suitable configurations for releasable engagement with the locking pin or other member on the powered injector 10. Those of ordinary skill in the art will appreciate that when the faceplate 112 is pivoted to the injection position (FIG. 1), the spring clip 140 automatically retainingly engages the locking pin 15 to retain the faceplate 112 in position. See FIG. 25 wherein the locking pin 15 is shown in phantom lines. To remove the faceplate 112, the user simply applies an upward force to the faceplate 112 to cause the spring clip 140 to disengage the locking pin 142 and permit the faceplate 112 to be rotated to a position wherein it can be removed from the pivot pin 132. In another embodiment shown in FIG. 23, the spring clip 140 is replaced with a conventional spring-biased ball detent assembly 150 that is adapted to engage the end of the locking pin 15 when the faceplate 110 is in the injection position to apply a releasable retention force thereto. See FIG. 26 wherein the locking pin 15 is shown in phantom lines. Those of ordinary skill in the art will understand that the locations of these locking components may also be reversed. That is, the locking pin 15 may be provided on the rear face of the faceplate 112 and the spring clip 140 or ball detent assembly 150 could be mounted to the housing 12.

Figure 27:
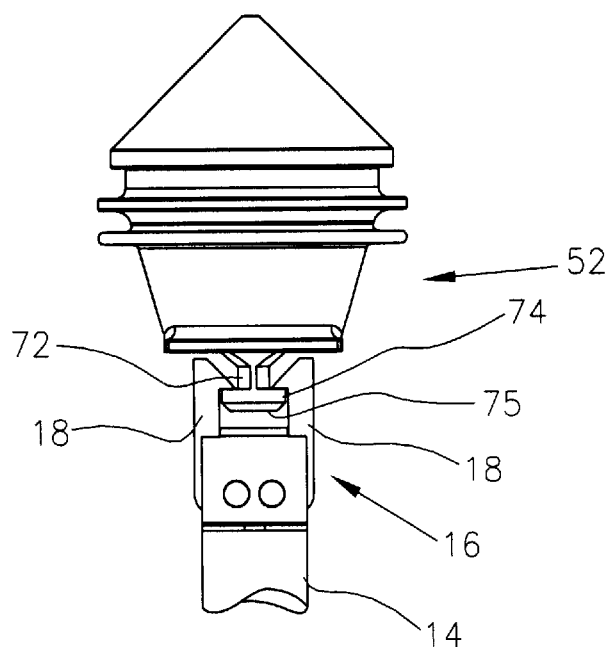
FIG. 27 is a partial view of the initial engagement of a plunger with the plunger attachment assembly of a powered injector.
Figure 28:
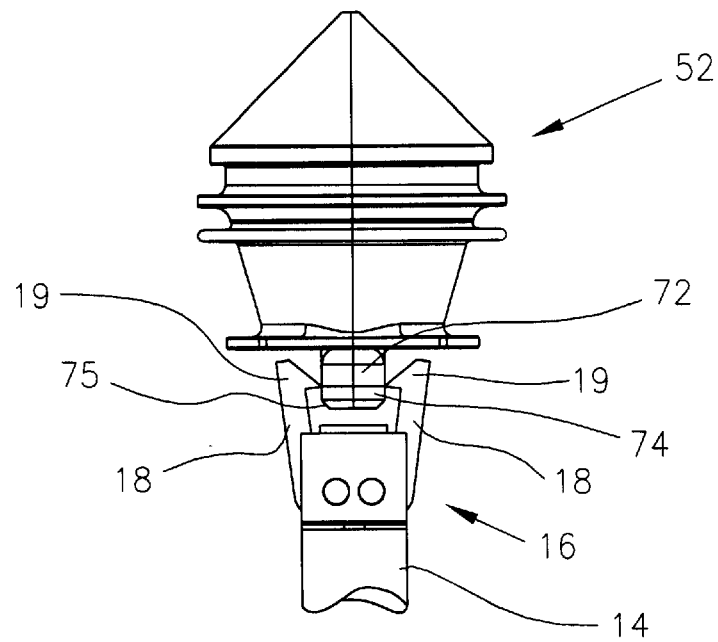
FIG. 28 is a partial view of the plunger and plunger attachment assembly after the plunger has been moved to an engaged position.

After the faceplate 112 has been attached to the powered injector 10, the plunger drive member 14 is advanced to a position wherein the plunger attachment assembly 16 may engage the rear plunger attachment portion 70 of a syringe 30 that is attached to the faceplate 112 in the above-described manner. The reader will appreciate that the assembly method described above for installing a plunger with a syringe can be employed to orient the plunger such that the attachment button may be coupled to the plunger attachment assembly after the syringe has been affixed to the faceplate 112 in the above-described manner. FIG. 27 depicts the position of the plunger 50 when syringe 30 is attached to the faceplate 112. When the plunger drive member 14 is advanced into the syringe body 32, the latch arms 18 that are pivotally affixed to the end of the plunger drive member 14 initially contact the attachment button 74 of the plunger 50 and pivot outward to enable the attachment button 74 to pass between the latch arms 18 as shown in FIG. 27. To facilitate smooth spreading of the latch arms 18, a chamfer 75 may be provided around the end of the attachment button 74. After the attachment button 74 has passed beyond the retainer catch 19 on each latch arm 18, the plunger core 52 is attached to the plunger drive 14. To release the plunger core 52 from the plunger drive member 14, the plunger core 52 is rotated (e.g., by rotating the syringe body 32) to bring the plunger blade portion 72 into contact with the latch arms 18 forcing them to an open position wherein the attachment button 74 may be withdrawn therefrom. See FIG. 28. As disclosed in U.S. Reissue Pat. No. 35,979, the contents of which are hereby incorporated by reference, the skilled artisan will appreciate that the unique cross-sectional shape of the attachment blade 72 also serves to facilitate smooth attachment and detachment of the plunger core 52 to the plunger drive member 14 at any position of the plunger 52 within the syringe 32 or at any time during an injection operation. This feature allows, among other things, the drive member 14 to be retracted relative to the plunger 52 after an injection operation has been completed, without retraction of the plunger 52. Those of ordinary skill in the art will also understand that rotation of the plunger core 52 in the above-mention manners occurs when the syringe 30 is detached from the faceplate 112.

Figure 29:
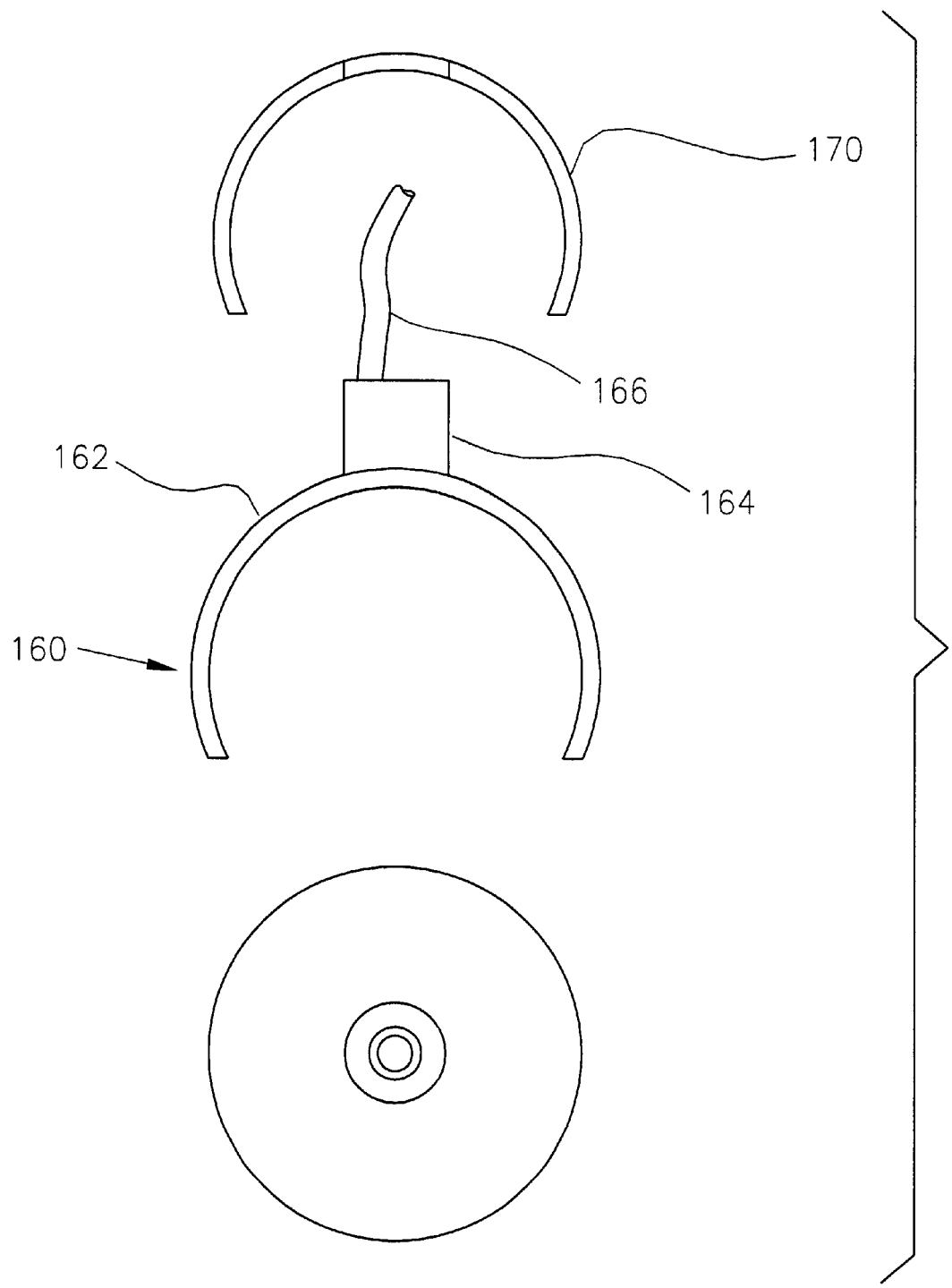
FIG. 29 is an exploded top assembly view of a syringe, a heater blanket and a sleeve of the present invention.
Figure 30:
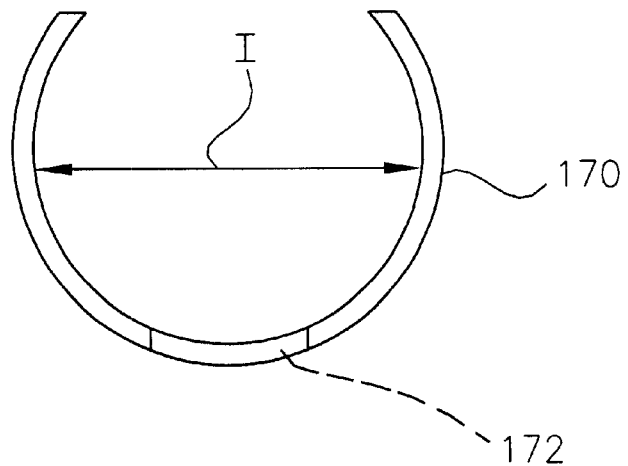
FIG. 30 is a front elevational view of a sleeve of the present invention.
Figure 31:
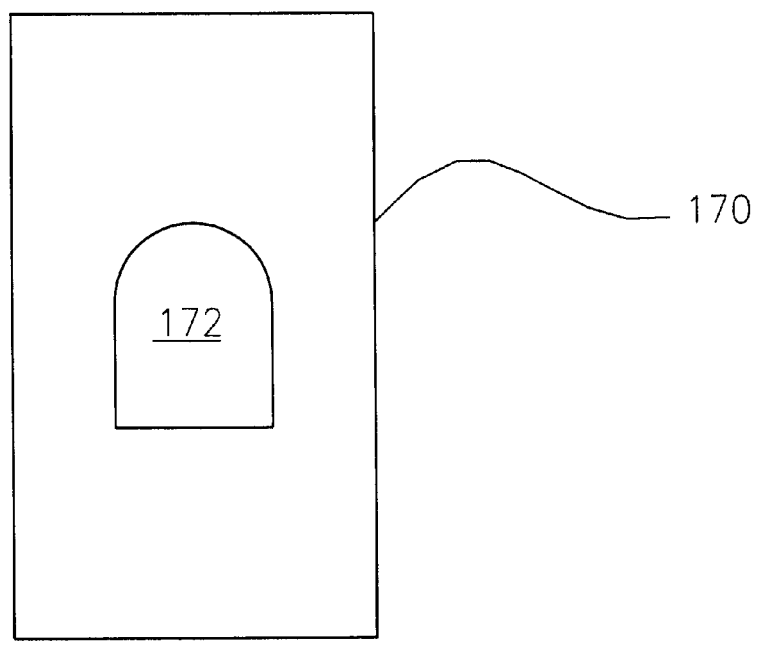
FIG. 31 is a plan view of the sleeve of FIG. 30.
Figure 32:
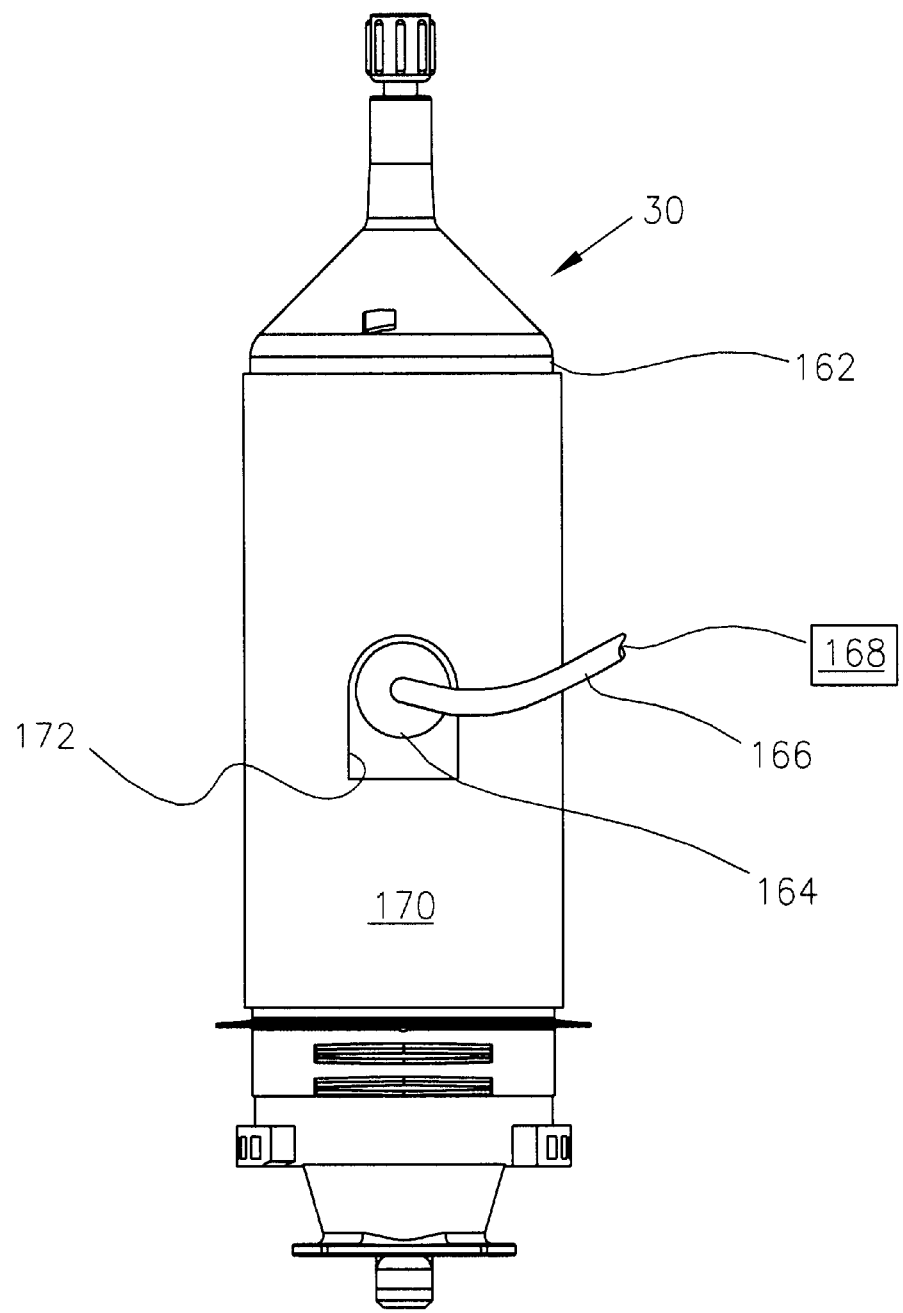
FIG. 32 is a side elevational assembly view of a syringe, a heater blanket and a sleeve of the present invention.

For injection procedures, it is often desirable to heat the fluid prior to injecting it into the patient. A conventional heater blanket 160 is commonly placed around the outer perimeter of the syringe body 32 to heat the fluid therein. The efficiency of the heater blanket 160 is dependent upon its close contact with the syringe body 32. In the past, therefore, the heater blanket 60 had to be sized to snap over the syringe body 32 in close contact therewith. Thus, the size of the heater blanket 60 was critical and heater blankets designed to snap onto a syringe 30 having one diameter were generally ill-suited for use with syringes 30 of smaller diameters. A conventional heater blanket is shown in FIG. 29. As can be seen in that Figure, such a heater blanket 160 has an arcuate resistance heater portion 162 and an attachment portion 164 that facilitates attachment of a power cable 166 to the heater portion 162. The power cable 166 is then connected to a source of electricity 168. See FIG. 32. One embodiment of the present invention includes an arcuate "split" sleeve member 170. As used herein, the term "split" means that the sleeve when viewed from an end is not continuous. As can be seen in FIGS. 30 and 31, the sleeve member 170 comprises an arcuate segment that has an internal diameter "I" that is less than the outer diameter of the smallest syringe with which the sleeve 170 is to be used. See FIG. 30. In one embodiment, the sleeve 170 is fabricated from a rigid material that permits a desired amount of flexure. In this embodiment, sleeve may be fabricated from polypropylene plastic or other injection molded polymeric material. For example, a sleeve 170 having an inner diameter of 2.0 inches may be able to support a heater 160 on a syringe body 32 having a diameter of 2.250 inches. That same sleeve 170 could also conceivably support a heater 160 on a syringe body 32 with a diameter of 2.0 inches. As can also be seen in FIGS. 30 and 31, the sleeve 170 is provided with an aperture 172 that is sized to permit the attachment portion 164 of the heater 160 to protrude therethrough. The reader will appreciate that the shape of the aperture 172 shown in FIG. 31 can accommodate round and square-shaped attachment portions 164. To use the sleeve 170 of the present invention, the resistance heater 162 is placed around the body 32 of the syringe 30 and the sleeve 170 is then snapped around the heater 160 to clampingly retain it in close engagement with the syringe body 32. See FIG. 32.

Thus, from the foregoing discussion, it is apparent that many of the problems encountered by prior syringes and powered injectors are solved by the present invention. Those of ordinary skill in the art will, of course, appreciate that various changes in the details, materials and arrangement of parts which have been herein described and illustrated in order to explain the nature of the invention may be made by the skilled artisan within the principle and scope of the invention as expressed in the appended claims.

What is claimed is:

1. A syringe, comprising:
   a syringe body defining a syringe axis and having an open rear end, an interior surface and a discharge end; and
   a plunger slidably received in said syringe body and selectively axially movable therein, said plunger having a seal comprising at least one sealing rib on an outer circumference thereof for establishing a substantially fluid-tight seal with the interior surface of said syringe body, said plunger further having an anti-cocking member formed thereon for maintaining said plunger in substantial axial alignment with the syringe axis and the at least one sealing rib in sealing contact with the interior surface of said syringe body, the anti-cocking member being dimensioned such that the anti-cocking member does not contact the interior surface of said syringe body when said plunger is in substantial axial alignment with the syringe axis, said plunger further having a drive engagement member formed thereon for connecting the plunger to a drive mechanism.

2. The syringe of claim 1 wherein said plunger further has an alignment flange formed thereon.

3. The syringe of claim 1 wherein the syringe body comprises at least one attachment flange.

4. The syringe of claim 1 wherein the syringe body comprises at least a first pair of attachment flanges.

5. The syringe of claim 4 wherein the syringe body further comprises at least a second pair of attachment flanges.

6. The syringe of claim 5 wherein the second pair of attachment flanges is arranged at 90° with respect to the first pair of attachment flanges.

7. The syringe of claim 1 wherein the syringe body comprises an annular drip flange formed around an outer perimeter thereof.

8. The syringe of claim 3 wherein the syringe body further comprises an annular drip flange positioned forward of the at least one attachment flange.

9. The syringe of claim 3 wherein the at least one attachment flange comprises two attachment flanges.

10. The syringe of claim 1 wherein the syringe body is formed of polypropylene.

11. The syringe of claim 1 wherein the syringe body is prefilled with a fluid medium.

12. The syringe of claim 1 wherein the discharge end defines a screw-threaded connection portion to facilitate attachment of a connector tubing to the discharge end.

13. The syringe of claim 1 wherein the anti-cocking member is disposed rearward of the at least one sealing rib.

14. The syringe of claim 1 wherein the anti-cocking member comprises a ring extending around the perimeter of said plunger.

15. The syringe of claim 1 wherein an outer perimeter of the anti-cocking member is rounded.

16. A syringe comprising a plunger defining a central axis and comprising an attachment portion connecting the plunger to a drive mechanism, the attachment portion comprising a blade portion having a height and an attachment button having a diameter, said attachment button attached to said blade portion and being substantially perpendicular to the central axis, the height of said blade portion being substantially equal to the diameter of said attachment button.

17. The syringe of claim 16 wherein the plunger attachment portion allows the plunger to be connected to or disconnected from a drive member of an injector at any location of the plunger within the syringe.

18. The syringe of claim 16, further comprising a syringe body in which the plunger is movably disposed.

19. The syringe of claim 18 wherein the syringe body comprises at least one attachment flange.

20. The syringe of claim 18 wherein the syringe body comprises at least a first pair of attachment flanges.

21. The syringe of claim 20 wherein the syringe body further comprises at least a second pair of attachment flanges.

22. The syringe of claim 21 wherein the second pair of attachment flanges is arranged at 90° with respect to the first pair of attachment flanges.

23. The syringe of claim 19 wherein the syringe body further comprises an annular drip flange positioned forward of the at least one attachment flange.

24. The syringe of claim 19 wherein the at least one attachment flange comprises two attachment flanges.

25. The syringe of claim 18 wherein the syringe body comprises an annular drip flange formed around an outer perimeter thereof.

26. The syringe of claim 18 wherein the syringe body is formed of polypropylene.

27. The syringe of claim 18 wherein the syringe body is prefilled with a fluid medium.

28. The syringe of claim 18 wherein the syringe body has a discharge end that defines a screw-threaded connection portion to facilitate attachment of a connector tubing to the discharge end.

29. The syringe of claim 16 wherein said attachment button is substantially circular.

30. The syringe of claim 16 wherein said blade portion has a width that is less than the height.

31. The syringe of claim 16 wherein said blade portion has a hexagonal cross-sectional shape.

32. A syringe comprising:
a syringe body defining a syringe axis and having an interior surface, an open rear end and a discharge end;
a plunger movably disposed within the syringe body, the plunger comprising at least one sealing rib for establishing a substantially fluid-tight seal between said plunger and the interior surface of said syringe body, an anti-cocking member formed thereon to retain said plunger in axial alignment within said syringe body, and an attachment portion for connecting the plunger to a drive mechanism comprising a blade portion having a height and an attachment button having a diameter, the attachment button being attached to the blade portion, the height of the blade portion being substantially equal to the diameter of the attachment button.

33. The syringe of claim 32 wherein the blade portion is substantially perpendicular to a central axis of the plunger.

34. The syringe of claim 32 wherein the attachment portion of the plunger is operable to connect the plunger to a drive mechanism of an injector.

35. The syringe of claim 32 wherein the syringe body comprises at least one attachment flange.

36. The syringe of claim 32 wherein the syringe body comprises at least a first pair of attachment flanges.

37. The syringe of claim 36 wherein the syringe body further comprises at least a second pair of attachment flanges.

38. The syringe of claim 37 wherein the second pair of attachment flanges is arranged at 90° with respect to the first pair of attachment flanges.

39. The syringe of claim 32 wherein the syringe body comprises an annular drip flange formed around an outer perimeter thereof.

40. The syringe of claim 35 wherein the syringe body further comprises an annular drip flange positioned forward of the at least one attachment flange.

41. The syringe of claim 35 wherein the at least one attachment flange comprises two attachment flanges.

42. The syringe of claim 32 wherein the syringe body is formed of polypropylene.

43. The syringe of claim 32 wherein the syringe body is prefilled with a fluid medium.

44. The syringe of claim 32 wherein the discharge end defines a screw-threaded connection portion to facilitate attachment of a connector tubing to the discharge end.

45. The syringe of claim 32 wherein the anti-cocking member is disposed rearward of the at least one sealing rib.

46. The syringe of claim 32 wherein the anti-cocking member comprises a ring extending around the perimeter of the plunger.

47. The syringe of claim 32 wherein the attachment button is substantially circular.

48. The syringe of claim 32 wherein the blade portion has a width that is less than the height.

49. The syringe of claim 32 wherein the blade portion has a hexagonal cross-sectional shape.

50. The syringe of claim 32 wherein the anti-cocking member is dimensioned such that the anti-cocking member does not contact the interior surface of the syringe body when the plunger is in substantial axial alignment with the syringe axis.

51. A syringe comprising:
a syringe body defining a syringe axis and having an open rear end, an interior surface and a discharge end;
a plunger slidably received in said syringe body and selectively axially movable therein, said plunger having a seal comprising at least one sealing rib on an outer circumference thereof for establishing a substantially fluid-tight seal with the interior surface of said syringe body, said plunger further having an anti-cocking member formed thereon for maintaining said plunger in substantial axial alignment with the syringe axis and the at least one sealing rib in sealing contact with the interior surface of said syringe body, the anti-cocking member being dimensioned such that the anti-cocking member does not contact the interior surface of said syringe body when said plunger is in substantial axial alignment with the syringe axis, said plunger further having a drive engagement member formed thereon for connecting the plunger to a drive mechanism; and at least one attachment flange disposed on said syringe body.

52. A syringe comprising:

a syringe body defining a syringe axis and having an open rear end, an interior surface and a discharge end;

a plunger slidably received in said syringe body and selectively axially movable therein, said plunger having a seal comprising at least one sealing rib on an outer circumference thereof for establishing a substantially fluid-tight seal with the interior surface of said syringe body, said plunger further having an anti-cocking member formed thereon for maintaining said plunger in substantial axial alignment with the syringe axis and the at least one sealing rib in sealing contact with the interior surface of said syringe body, the anti-cocking member being dimensioned such that the anti-cocking member does not contact the interior surface of said syringe body when said plunger is in substantial axial alignment with the syringe axis, said plunger further having a drive engagement member formed thereon for connecting the plunger to a drive mechanism;

a first pair of attachment flanges disposed on said syringe body; and a second pair of attachment flanges disposed on said syringe body and arranged at approximately 90° with respect to said first pair of attachment flanges.

53. A syringe comprising:

a syringe body;

a plunger movably disposed within said syringe body, said plunger defining a central axis and comprising an attachment portion connecting the plunger to a drive mechanism, the attachment portion comprising a blade portion having a height and an attachment button having a diameter, the attachment button attached to the blade portion and being substantially perpendicular to the central axis, the height of the blade portion being substantially equal to the diameter of the attachment button; and at least one attachment flange disposed on said syringe body.

54. A syringe comprising:

a syringe body;

a plunger movably disposed within said syringe body, said plunger defining a central axis and comprising an attachment portion for connecting the plunger to a drive mechanism, the attachment portion comprising a blade portion having a height and an attachment button having a diameter, the attachment button attached to the blade portion and being substantially perpendicular to the central axis, the height of the blade portion being substantially equal to the diameter of the attachment button;

a first pair of attachment flanges disposed on said syringe body; and a second pair of attachment flanges disposed on said syringe body and arranged at approximately 90° with respect to said first pair of attachment flanges.

55. A syringe comprising:

a syringe body defining a syringe axis and having an interior surface, an open rear end and a discharge end;

a plunger movably disposed within said syringe body, said plunger comprising at least one sealing rib for establishing a substantially fluid-tight seal between said plunger and the interior surface of said syringe body, an anti-cocking member formed thereon to retain said plunger in axial alignment within said syringe body, and an attachment portion for connecting the plunger to a drive mechanism comprising a blade portion having a height and an attachment button having a diameter, the attachment button being attached to the blade portion, the height of the blade portion being substantially equal to the diameter of the attachment button; and at least one attachment flange disposed on said syringe body.

56. A syringe comprising:

a syringe body defining a syringe axis and having an interior surface, an open rear end and a discharge end;

a plunger movably disposed within said syringe body, said plunger comprising at least one sealing rib for establishing a substantially fluid-tight seal between said plunger and the interior surface of said syringe body, an anti-cocking member formed thereon to retain said plunger in axial alignment within said syringe body, and an attachment portion for connecting the plunger to a drive mechanism comprising a blade portion having a height and an attachment button having a diameter, the attachment button being attached to the blade portion, the height of the blade portion being substantially equal to the diameter of the attachment button;

a first pair of attachment flanges disposed on said syringe body; and a second pair of attachment flanges disposed on said syringe body and arranged at approximately 90° with respect to said first pair of attachment flanges.

* * * * *